United States Patent [19]

Hoechstetter et al.

[11] Patent Number: 5,426,226
[45] Date of Patent: Jun. 20, 1995

[54] INTERMEDIATES FOR MAKING RING-SUBSTITUTED 2-AMINO-1,2,3,4-TETRAHYDRONAPHTHA-LENES AND 3-AMINOCHROMANES

[76] Inventors: Craig S. Hoechstetter, 7128 Whitetail La., Apt. 2C, Indianapolis, Ind. 46254; Diane L. Huser, 5620 Broadway St., Indianapolis, Ind. 46220; John M. Schaus, 135 Raintree Dr., Zionsville, Ind. 46077; Robert D. Titus, 3639 Country Walk Cir., Indianapolis, Ind. 46227

[21] Appl. No.: 140,903

[22] Filed: Oct. 21, 1993

Related U.S. Application Data

[62] Division of Ser. No. 653,583, Feb. 8, 1991.

[51] Int. Cl.$^6$ .............................................. C07C 223/02
[52] U.S. Cl. .................................... 564/342; 564/340; 558/405
[58] Field of Search ................. 558/405; 564/340, 342

[56] References Cited

U.S. PATENT DOCUMENTS

| | | | |
|---|---|---|---|
| 4,801,605 | 1/1989 | Hutchinson | 514/432 |
| 4,873,262 | 10/1989 | Junge et al. | 514/510 |
| 5,196,454 | 3/1993 | Grauert | 514/654 |
| 5,214,156 | 5/1993 | Andersson | 549/75 |
| 5,286,753 | 2/1994 | Schaus | 514/657 |

FOREIGN PATENT DOCUMENTS

| | | | |
|---|---|---|---|
| 279150 | 8/1899 | European Pat. Off. | C07C 311/58 |
| 343830 | 11/1989 | European Pat. Off. | C07D 295/02 |
| 399982 | 11/1990 | European Pat. Off. | |
| WO81/03491 | 12/1981 | WIPO | C07C 93/14 |
| WO90/15047 | 5/1990 | WIPO | C07C 237/48 |
| WO91/09853 | 7/1991 | WIPO | C07D 311/58 |

OTHER PUBLICATIONS

Arvidsson et al "8-hydroxy-2-alkylamino tetralin and related compounds as central 5-H-tryptamine Receptor Agonists" J. Med Chem. 27 45-51 (1984).
Glennon, *J. Med. Chem.*, 30, 1-12 (1987).
CA, 110, 57322a (1989).

*Primary Examiner*—Celia Chang

[57] ABSTRACT

The present invention provides novel ring-substituted 2-amino-1,2,3,4-tetrahydronaphthalenes and 3-aminochromanes which exhibit binding activity at the serotonin 1A receptor. An intermediate for preparing the novel compounds have the following formula:

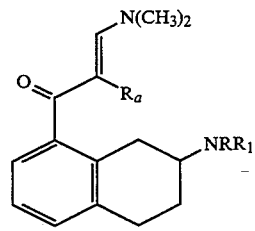

wherein R, $R_1$ and $R_9$, are as defined in the specification.

4 Claims, No Drawings

INTERMEDIATES FOR MAKING RING-SUBSTITUTED 2-AMINO-1,2,3,4-TETRAHYDRONAPHTHALENES AND 3-AMINOCHROMANES

This application is a division, of application Ser. No. 07/653,583, filed Feb. 8, 1991 pending.

BACKGROUND OF THE INVENTION

Over the last several years it has become apparent that the neurotransmitter serotonin (5-hydroxytryptamine—5-HT) is associated directly or indirectly with a number of physiological phenomena, including appetite, memory, thermoregulation, sleep, sexual behavior, anxiety, depression, and hallucogenic behavior [Glennon, R. A., *J. Med. Chem.* 30, 1 (1987)].

It has been recognized that there are multiple types of 5-HT receptors. These receptors have been classified as 5-$HT_1$, 5-$HT_2$, and 5-$HT_3$ receptors, with the former being further divided into the sub-classes 5-$HT_{1A}$, 5-$HT_{1B}$, 5-$HT_{1C}$, and 5-$HT_{1D}$.

Selected 2-amino-1,2,3,4-tetrahydronaphthalenes (2-aminotetralins) and 3-aminochromanes have been shown to exhibit binding affinity at the 5-$HT_{1A}$ receptor.

Co-pending application Ser. No. 315,750 filed Feb. 27, 1989, describes certain 2-aminotetralins substituted in the 8-position by formyl, cyano, halo, hydroxymethyl, carboxamido, carboxyl, or alkoxycarbonyl. The compounds are described as exhibiting high binding affinity at the 5-$HT_{1A}$ receptor. In addition, co-pending application Ser. No. 315,752 filed Feb. 27, 1989, describes other 2-aminotetralins substituted in the 8-position and 3-aminochromanes substituted in the 5-position by sulfides, sulfoxides, and sulfones. These compounds, as well, are described as having binding affinity at the 5-$HT_{1A}$ receptor. A further class of 2-aminotetralins substituted in the 8-position and 3-aminochromanes substituted in 5-position by an acyl group and having 5-$HT_{1A}$ agonist activity is described in co-pending application Ser. No. 567,985 filed Aug. 15, 1990. Another class of 2-aminotetralins are described in European Patent Application No. 343,830, published Nov. 29, 1989. These compounds have a piperazinyl or homopiperazinyl moiety in the 2-position and, distinct from the foregoing tetralins, exhibit serotonin re-uptake inhibition as opposed to serotonin receptor binding affinity. We have now discovered a further class of compounds which, by reason of their 5-$HT_{1A}$ activity, are useful in the treatment, for example, of sexual dysfunction, anxiety, depression, and eating disorders, such as anorexia.

SUMMARY OF THE INVENTION

The present invention provides novel ring-substituted 2-amino-1,2,3,4-tetrahydronaphthalenes and 3-aminochromanes which have agonist partial agonist and antagonist activity at the 5-$HT_{1A}$ receptor.

More specifically, this invention relates to a compound of the formula

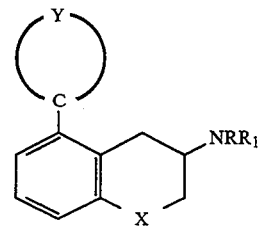

in which R is $C_1$–$C_4$ alkyl, allyl, or cyclopropylmethyl;
$R_1$ is hydrogen, $C_1$–$C_4$ alkyl, allyl, cyclopropylmethyl, or aryl($C_1$–$C_4$-alkyl);
X is —$CH_2$— or —O—;
Y, in combination with the carbon atom to which it is joined, defines a substituted or unsubstituted aromatic heterocyclic 5- or 6-membered ring, said ring having from one to three heteroatoms which are the same or different and which are selected from the group consisting of sulfur, oxygen, and nitrogen; and, when Y contains two adjacent carbon atoms, the adjacent carbon atoms may be structured to form, in conjunction with a group of the formula —CH=CH—CH=CH—, a fused benzene ring, provided, however, that (1) when the heterocyclic ring contains 5 members, the heteroatoms comprise not more than one sulfur or one oxygen atom but not both; (2) when the heterocyclic ring contains 6 members, sulfur and oxygen are not present; and (3) when the heterocyclic ring contains a sulfur or oxygen atom, the benzofusion, if present, is joined to a carbon adjacent to said sulfur or oxygen atom;
and pharmaceutically acceptable acid addition salts thereof.

This invention also provides a pharmaceutical formulation which comprises, in association with a pharmaceutically acceptable carrier, diluent, or excipient, a compound of the formula

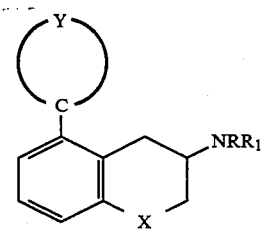

in which R is $C_1$–$C_4$ alkyl, allyl, or cyclopropylmethyl;
$R_1$ is hydrogen, $C_1$–$C_4$ alkyl, allyl, cyclopropylmethyl, or aryl($C_1$–$C_4$-alkyl);
X is —$CH_2$— or —O—;
Y, in combination with the carbon atom to which it is joined, defines a substituted or unsubstituted aromatic heterocyclic 5- or 6-membered ring, said ring having from one to three heteroatoms which are the same or different and which are selected from the group consisting of sulfur, oxygen, and nitrogen; and, when Y contains two adjacent carbon atoms, the adjacent carbon atoms may be structured to form, in conjunction with a group of the formula —CH=CH—CH=CH—, a fused benzene ring, provided, however, that (1) when the heterocyclic ring contains 5 members, the heteroatoms comprise not more than one sulfur or one oxygen atom but not both; (2) when the heterocyclic ring contains 6 members, sulfur and oxygen are not present; and (3) when the heterocyclic ring contains a sulfur or oxygen atom, the benzofusion, if present, is joined to a carbon adjacent to said sulfur or oxygen atom;

and pharmaceutically acceptable acid addition salts thereof.

A further embodiment of the invention is a method for modulating a biological response at the 5-HT$_{1A}$ receptor. More particularly, further embodiments are methods for treating a variety of disorders which may be treated by modulation of the 5-HT$_{1A}$ receptor in mammals. Included among these disorders are anxiety, depression, sexual dysfunction, gastrointestinal disorders, hypertension, and eating disorders. Any of these methods employ a compound of the formula

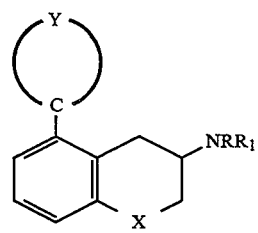

in which R is $C_1$–$C_4$ alkyl, allyl, or cyclopropylmethyl;
R$_1$ is hydrogen, $C_1$–$C_4$ alkyl, allyl, cyclopropylmethyl, or aryl ($C_1$–$C_1$-alkyl );
X is —CH$_2$— or —O—;
Y, in combination with the carbon atom to which it is joined, defines a substituted or unsubstituted aromatic heterocyclic 5- or 6-membered ring, said ring having from one to three heteroatoms which are the same or different and which are selected from the group consisting of sulfur, oxygen, and nitrogen; and, when Y contains two adjacent carbon atoms, the adjacent carbon atoms may be structured to form, in conjunction with a group of the formula —CH=CH—CH=CH—, a fused benzene ring, provided, however, that (1)when the heterocyclic ring contains 5 members, the heteroatoms comprise not more than one sulfur or one oxygen atom but not both; (2) when the heterocyclic ring contains 6 members, sulfur and oxygen are not present; and (3) when the heterocyclic ring contains a sulfur or oxygen atom, the benzofusion, if present, is joined to a carbon adjacent to said sulfur or oxygen atom;

and pharmaceutically acceptable acid addition salts thereof.

DETAILED DESCRIPTION OF THE INVENTION

In the above formulas, the term "$C_1$-$C_4$ alkyl" means a straight or branched alkyl chain having from one to four carbon atoms. Such $C_1$-$C_4$ alkyl groups are methyl, ethyl, R-propyl, isopropyl, R-butyl, isobutyl, sec-butyl, and t-butyl.

The term "aryl($C_1$-$C_4$ alkyl)" means an aromatic carbocyclic structure joined to a $C_1$-$C_4$ alkyl group. Examples of such groups are benzyl, phenylethyl, α-methylbenzyl, 3-phenylpropyl, α-naphthylmethyl, β-naphthylmethyl, 4-phenylbutyl, and the like.

As noted, the group

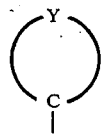

defines substituted and unsubstituted aromatic heterocyclic 5- and 6-membered rings as well as rings having a benzene moiety fused thereto. Preferably, these groups have a heteroatom joined to the carbon bonded to the tetralin ring. Thus, the group Y preferably has the sequence —V—W— in which V is selected from the group consisting of sulfur, oxygen and nitrogen; and W is a chain 3 or 4 atoms in length, said atoms being selected from the group consisting of carbon, sulfur, oxygen, and nitrogen. When V is nitrogen, the nitrogen atom may be joined to the carbon bonded to the tetralin ring by a single or double bond.

Examples of unsubstituted 5- and 6-membered aromatic heterocyclic rings are the following:

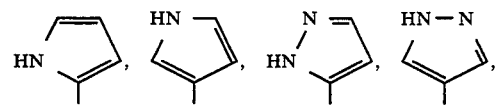

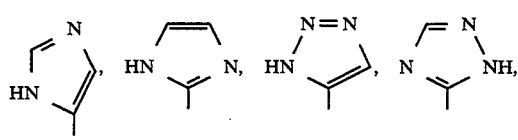

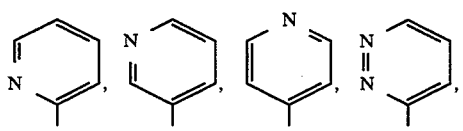

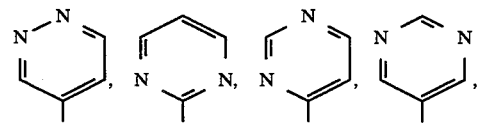

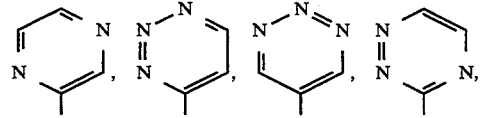

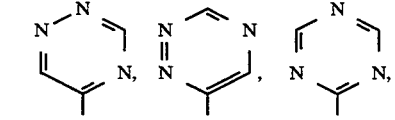

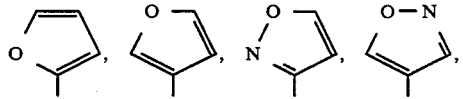

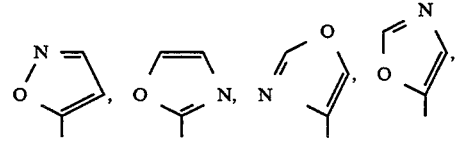

-continued

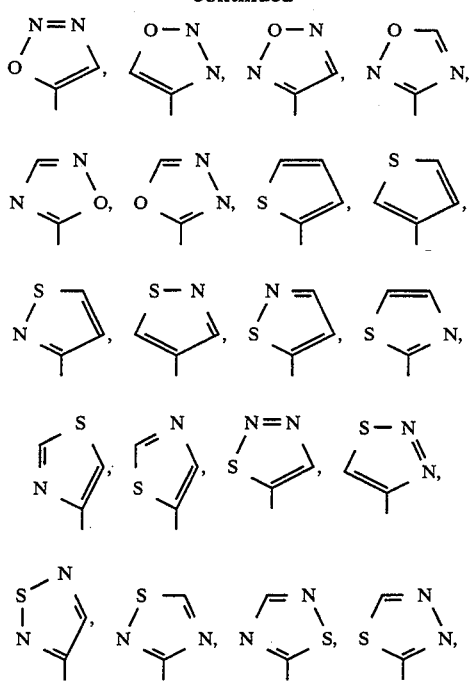

and the like. It will be appreciated that certain of the heterocycles, including many of the foregoing, may exist in tautomeric forms. Although only one form is presented in the foregoing, all such forms are included within the scope of this invention.

Moreover, it will be appreciated from the foregoing examples that a number of the ring structures have adjacent carbons within the definition of the group Y. In accordance with this invention, the adjacent carbons can be joined to form a fused phenyl ring giving rise, for example, to structures such as benzo[d]isoxazole, indole, benzofuran, benzo[b]thiophene, quinoline, isoquinoline, benzoisoxazole, benzothiazole, benzoimidazole, and the like.

Moreover, the aromatic heterocyclic 5- or 6-membered ring, as well as its companion benzo-fused structure, may have the hydrogen present on any nitrogen or carbon in the ring structure replaced by any of a wide range of recognized substitution groups. When the substitution is at a ring nitrogen, the substitution preferably is selected from $C_1$–$C_4$ alkyl, phenyl, or phenyl-($C_1$–$C_4$ alkyl). When the substitution is at a ring carbon, including the carbons of a benzo-fused system, the substitution preferably is selected from $C_1$–$C_4$ alkyl, $C_1$–$C_4$ alkoxy, $C_1$–$C_4$ thioalkyl, hydroxy, halo, amino, cyano, or phenyl.

Multiple substitutions are included within the scope of this invention. Thus, two or more carbons and/or nitrogens, when available for substitution, can be substituted as described in the foregoing. Preferably, however, if ring-substitution is present, the ring is mono- or di-substituted.

In the foregoing, the term "$C_1$–$C_4$ alkyl" is as defined hereinbefore. The term "$C_1$–$C_4$ alkoxy" means any of methoxy, ethoxy, n-propoxy, isopropoxy, n-butoxy, isobutoxy, sec-butoxy, and t-butoxy. The term "halo" means any of fluoro, chloro, bromo, and iodo; and the term "$C_1$–$C_4$ thioalkyl" means any of methylthio, ethylthio, n-propylthio, isopropylthio, n-butylthio, isobutylthio, sec-butylthio, and t-butylthio.

The term "aryl" means an aromatic carbocyclic structure. Examples of such ring structures are phenyl, naphthyl, and the like.

Examples of groups defined by the moiety

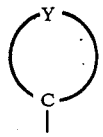

are fur-2-yl, fur-3-yl, 2-methoxyfur-3-yl, thien-2-yl, thien-3-yl, 3-chlorothien-2-yl, pyrrol-2-yl, pyrrol-3-yl, 3-phenylpyrrol-2-yl, 2-isopyrrol-2-yl, 2-isopyrrol-3-yl, pyrazol-3-yl, imidazol-2-yl, 1,2,3-triazol-4-yl, 1,2,4-triazol-3-yl, isoxazol-4-yl, isoxazol-3-yl, isoxazol-5-yl, oxazol-2-yl, thiazol-5-yl, isothiazol-4-yl, 1,2,4-oxadiazol-5-yl, 5-methyl-1,2,4-oxadiazol-3-yl, 3-hydroxy-1,2,5-oxadiazol-4-yl, 2-bromo-1,3,4-oxadiazol-5-yl, 3-methyl-1,2,4-dioxazol-5-yl, pyridin-4-yl, pyridazin-3-yl, 5-methylthiopyrimidin-4-yl, pyrazin-2-yl, 1,3,5-triazin-2-yl, 1,2,4-triazin-3-yl, 1,2,3-triazin-4-yl, benzofuran-2-yl, benzothiofuran-3-yl, indol-2-yl, indol-3-yl, indazol-3-yl, indoxazin-3-yl, benzoxazol-2-yl, anthranil-3-yl, quinolin-2-yl, isoquinolin-3-yl, 1,2-benzodiazin-3-yl, 1,3-benzodiazin-2-yl, and the like.

While all of the compounds of the present invention are useful for treating a variety of disorders by virtue of their ability to modulate the function of the 5-HT$_{1A}$ receptor in mammals, certain of the compounds are preferred.

Thus, R and $R_1$ preferably are both $C_1$–$C_4$ alkyl, and, more preferably, both are n-propyl.

The group

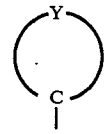

preferably is a substituted or unsubstituted isoxazolyl and is more preferably a substituted or unsubstituted isoxazol-3-yl or isoxazol-5-yl group.

The compounds of the present invention possess an asymmetric carbon represented by the carbon atom labeled with an asterisk in the following formula:

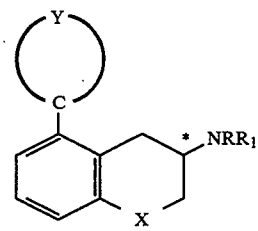

As such, each of the compounds exists as its individual d- and l-stereoisomers and also as the racemic mixture of such isomers. Accordingly, the compounds of the present invention include not only the dl-racemates but also their respective optically active d- and l-isomers.

As mentioned hereinabove, the invention includes pharmaceutically acceptable acid addition salts of the compounds defined by the above formula. Since the compounds of this invention are amines, they are basic in nature and accordingly react with any of a number of inorganic and organic acids to form pharmaceutically acceptable acid addition salts. Since the free amines of the compounds of this invention are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included as compounds of this invention.

The following compounds further illustrate compounds contemplated within the scope of this invention:

2-(Di-n-propylamino)-8-(isothiazol-3-yl)-1,2,3,4-tetrahydronaphthalene;
2-Ethylamino-8-(isoxazol-3-yl)-1,2,3,4-tetrahydronaphthalene;
2-(N-Methyl-N-benzylamino)-8-(5-n-propyl-1,2,3-oxadiazol-4-yl)-1,2,3,4-tetrahydronaphthalene;
2-Diallylamino-8-(pyrazol-3-yl)-1,2,3,4-tetrahydronaphthalene;
2-Diethylamino-8-(1,3,4-oxadiazol-2-yl)-1,2,3,4-tetrahydronaphthalene;
2-(Di-n-propylamino)-8-(3-methoxypyrid-2-yl)1,2,3,4-tetrahydronaphthalene;
2-Benzylmethylamino-8-(benzofuran-2-yl)-1,2,3,4-tetrahydronaphthalene;
2-(Di-n-propylamino)-8-(1,3,5-triazin-2-yl)-1,2,3,4-tetrahydronaphthalene;
2-Dimethylamino-8-(benzoxazol-2-yl)-1,2,3,4-tetrahydronaphthalene;
2-(Di-cyclopropylmethylamino)-8-(oxazol-4-yl)-1,2,3,4-tetrahydronaphthalene;
2-(Di-n-propylamino)-8-(1,2,5-oxadiazol-4-yl)-thio-1,2,3,4-tetrahydronaphthalene;
2-Ethylamino-8-(furan-2-yl)-1,2,3,4-tetrahydronaphthalene;
2-n-Butylamino-8-(5-methoxypyrimidin-2-yl)-1,2,3,4-tetrahydronaphthalene;
2-(Di-n-propylamino)-8-(5-chlorooxazol-2-yl)-1,2,3,4-tetrahydronaphthalene;
2-(Di-n-propylamino)-8-(1,2,4-oxadiazol-3-yl)-1,2,3,4-tetrahydronaphthalene;
3-(Di-n-propylamino)-5-(isoxazol-3-yl)-chromane;
3-(Di-n-propylamino)-5-(isoxazol-5-yl)-chromane;
2-(Di-n-propylamino)-8-(indol-3-yl)-1,2,3,4-tetrahydronaphthalene;
2-(Di-n-propylamino)-8-(benzoxazol-2-yl)-1,2,3,4-tetrahydronaphthalene;
2-(Di-n-propylamlno)-8-(benzothiazol-2-yl)-1,2,3,4-tetrahydronaphthalene
2-(Di-n-propylamlno)-8-(1,3,4-thiadiazol-2-yl)-1,2,3,4-tetrahydronaphthalene;
2-(Di-n-propylamino)-8-(6-bromopyrazin-2-yl)-1,2,3,4-tetrahydronaphthalene;
2-(Di-n-propylamlno)-8-(pyrazin-2-yl)-1,2,3,4-tetrahydronaphthalene;
2-(Di-n-propylamino)-8-(oxazol-2-yl)-1,2,3,4-tetrahydronaphthalene;
2-(Di-n-propylamino)-8-(pyrazol-5-yl)-1,2,3,4-tetrahydronaphthalene;
2-(Di-n-propylamino)-8-(3-methyl-1,2,4-oxadiazol-5-yl))-1,2,3,4-tetrahydronaphthalene;
2-(Di-n-propylamino)-8-(3-phenyl-1,2,4-oxadiazol-5-yl)-1,2,3,4-tetrahydronaphthalene;
2-(Di-n-propylamino)-8-(2-aminopyrimidin-4-yl)thio-1,2,3,4-tetrahydronaphthalene;
2-(Di-n-propylamino)-8-(pyrimidin-2-yl)-1,2,3,4-tetrahydronaphthalene;
2-(Di-n-propylamino)-8-(pyrimidin-4-yl)-1,2,3,4-tetrahydronaphthalene;
2-(Di-n-propylamino)-8-(pyrimidin-5-yl)-1,2,3,4-tetrahydronaphthalene;
2-(Di-n-propylamino)-8-(benzimidazol-2-yl)-1,2,3,4-tetrahydronaphthalene; and the like.

The compounds of the present invention may be prepared by procedures well known to those of ordinary skill in the art. The compounds in which X is —CH$_2$— may be synthesized via an 8-bromo-2-tetralone. The 8-bromo-2-tetralone then is reductively aminated with the desired amine to produce the desired 2-amino-8-bromotetralin intermediate. The 8-bromo intermediate then can be used in any of a wide variety of sequences to produce a compound of this invention.

The compounds of this invention in which X is oxygen are available as in the foregoing, but using a 5-substituted 3-chromanone. This molecule can be produced by a sequence of reactions beginning with m-bromophenol. Briefly, m-bromophenol is treated with allyl bromide in the presence of potassium carbonate to produce allyl 3-bromophenyl ether. The ether is converted to 2-allyl-3-bromophenol upon heating it in the presence of N,N-dimethylaniline. The phenol, upon reaction with ethyl chloroacetate, is converted to the ethyl ester of 2-allyl-3-(carboxymethoxy)bromobenzene. Upon oxidation using ozone followed by reductive work up, the allyl group is converted to a formylmethyl substituent which is then further oxidized using Jones' Reagent to the carboxymethyl substituent, the resulting product being the ethyl ester of (2-carboxymethyl-3-bromo)phenoxyacetic acid. The carboxylic acid group of this compound is esterified with t-butyl acetate and concentrated H$_2$SO$_4$ to form the ethyl ester of 3-bromo-2-(carbo-t-butoxymethyl)phenoxyacetic acid. In the presence of potassium t-butoxide, the diester is cyclized to form 4-t-butoxy-carbonyl-5-bromo-3-chromanone.

Upon stirring at room temperature in the presence of acid, the latter is converted to 5-bromo-3-chromanone.

Compounds of this invention may be synthesized by reacting a halo (or trifluoromethylsulfonoxy) heterocyclic compound (optionally bearing additional substituents) with a compound of the formula

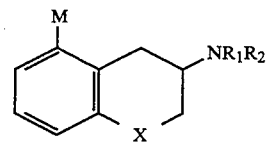

where M is Li, Mg(halo), Sn(alkyl)$_3$, Zn(halo), Hg(halo) or BO$_2$H$_2$ in the presence of a palladium or nickel catalyst such as Pd(PPh$_3$)$_4$, PdCl$_2$, Pd(PPh$_3$)$_2$Cl$_2$, nickel acetylacetonate, NiCl$_2$(PPh$_3$)$_2$, and the like.

The lithium and magnesium reagents are prepared by reaction of the appropriate chloro, bromo, or iodo substituted compound with an organolithium reagent and magnesium metal, respectively, in a solvent such as ether or tetrahydrofuran. The zinc, tin, and mercury reagents are prepared by reaction of the lithiated heterocycle with a zinc, tin, or mercury derivative such as zinc chloride, chlorotrialkylstannane, or mercuric chloride. The boronic acid derivative is prepared by reacting the lithium reagent with trimethylborate and acid hydrolysis of the resulting boronate ester.

Alternatively, an organometallic reagent derived from the heterocycle (and optionally bearing additional substituents) may be reacted with a compound of the formula

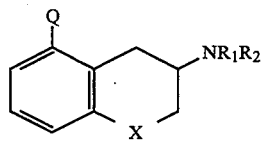

in which Q is bromo, iodo, or trifluoromethylsulfonyl, in the presence of a palladium or nickel catalyst such as Pd(PPh$_3$)$_4$, PdC$_2$, Pd(PPh$_3$)$_2$Cl$_2$, nickel acetylacetonate, NiCl$_2$(PPh$_3$)$_2$, and the like.

The metal in the organometallic derivative of the heterocycle may be lithium, magnesium (Grignard reagent), zinc, tin, mercury, or a boronic acid (—BO$_2$H$_2$). The lithium and magnesium reagents are prepared by reaction of the appropriate chloro, bromo, or iodo substituted heterocycle with an organolithium reagent and magnesium metal, respectively. Alternatively, the lithiated heterocyctes may be prepared by treating a heterocycle with a strong base such as an alkyllithium or lithium diisopropylamide. The zinc, tin, and mercury reagents are prepared by reaction of the lithiated heterocycle with a zinc, tin, or mercury derivative such as zinc chloride, chlorotrialkylstannane, or mercuric chloride. The boronic acid derivative is prepared by reacting the lithium reagent with trimethylborate and acid hydrolysis of the resulting boronate ester.

Also, the compounds of this invention having a five membered heterocyclic ring may be prepared by cycloaddition of a compound of the formula

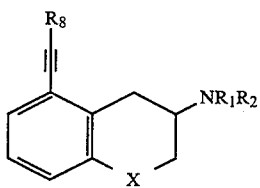

(1) with a 1,3 dipole of the following type:

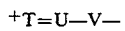

$^+$T=U—V— where T, U, and V are selected from the following list:

| T | U | V |
|---|---|---|
| CR$_8$ | N | CHR$_8$ |
| CR$_8$ | N | NR$_9$ |
| CR$_8$ | N | O |
| N | N | O |
| CR$_8$ | CR$_8$ | NR$_9$ |
| CR$_8$ | CR$_8$ | O |
| N | CR$_8$ | CR$_8$ |
| N | CR$_8$ | NR$_9$ |
| N | CR$_8$ | O | to give products of the following type:

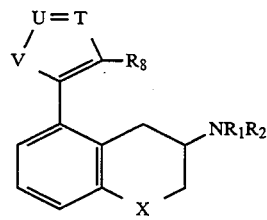

or (2) with a 1,3 dipole of the following type:

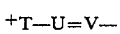

$^+$T—U=V— where T, U, and V are selected from the following list:

| T | U | V |
|---|---|---|
| CHR$_8$ | N | N |
| NR$_9$ | N | N | to give products of the following type:

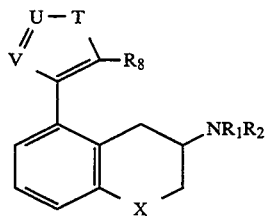

In the foregoing, R$_8$ preferably is any of hydrogen, C$_1$-C$_4$ alkyl, C$_1$-C$_4$ alkoxy, C$_1$-C$_4$ thioalkyl, hydroxy, halo, amino, cyano and phenyl, and R$_9$ preferably is any of hydrogen, C$_1$-C$_4$ alkyl, phenyl, and phenyl(C$_1$-C$_4$ alkyl).

The compounds of this invention are available by a number of general reactions. General schemes are provided in the following; in each, the groups $R_a$, $R_b$, and $R_c$ are as follows.

$R_a$—hydrogen, $C_1$–$C_4$ alkyl, halogen, OH, O($C_1$–$C_4$ alkyl), S($C_1$–$C_4$ alkyl), $NH_2$, CN, or phenyl;

$R_b$—hydrogen, $C_1$–$C_4$ alkyl, phenyl, or ($C_1$–$C_4$ alkyl)-phenyl;

$R_c$—hydrogen or $C_1$–$C_3$ alkyl.

Pyrazole

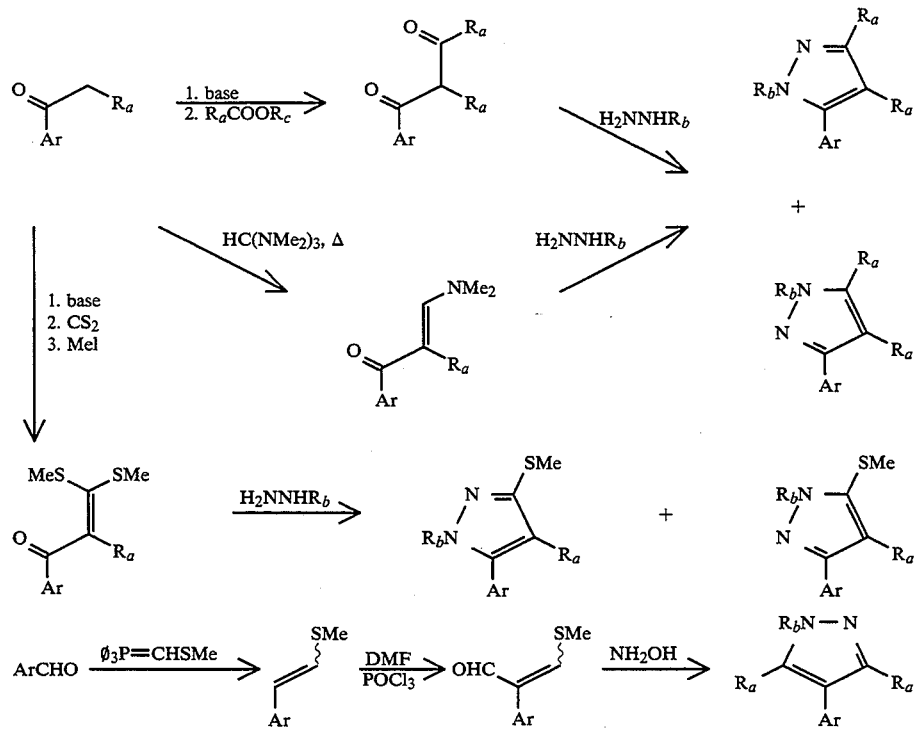

Imidazole (1)

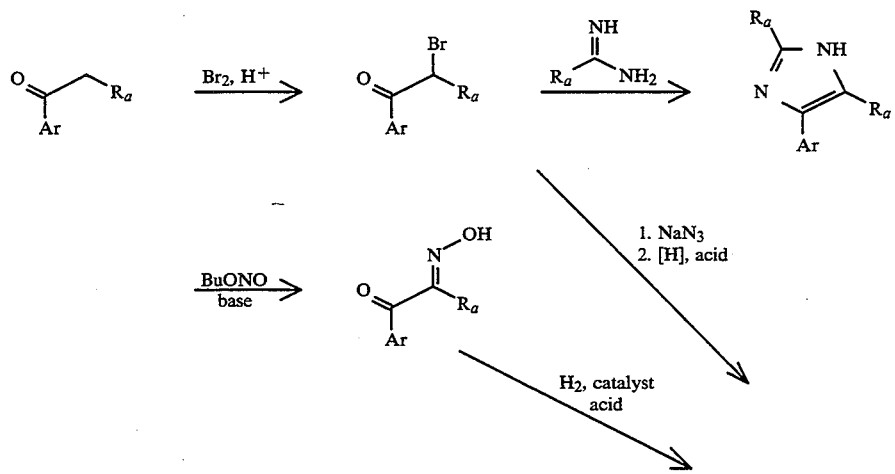

-continued
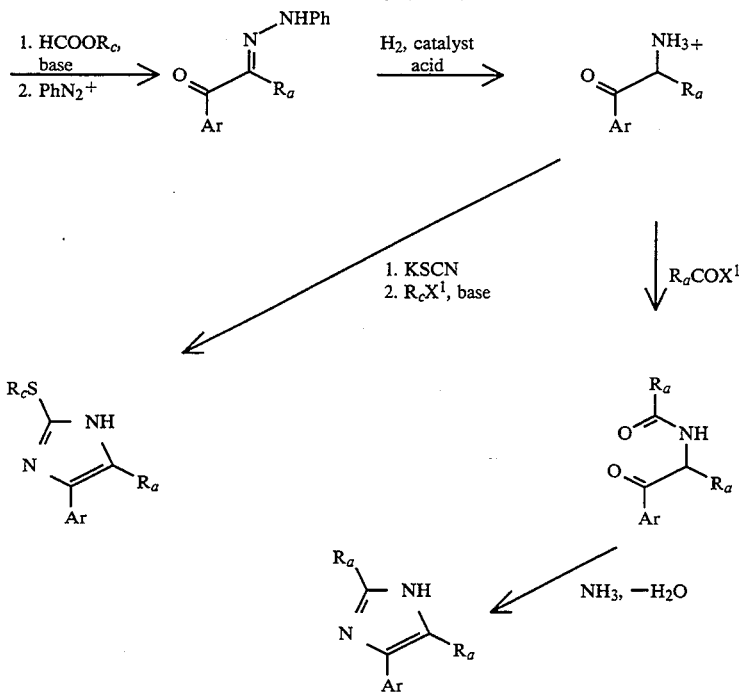
Imidazole (2)
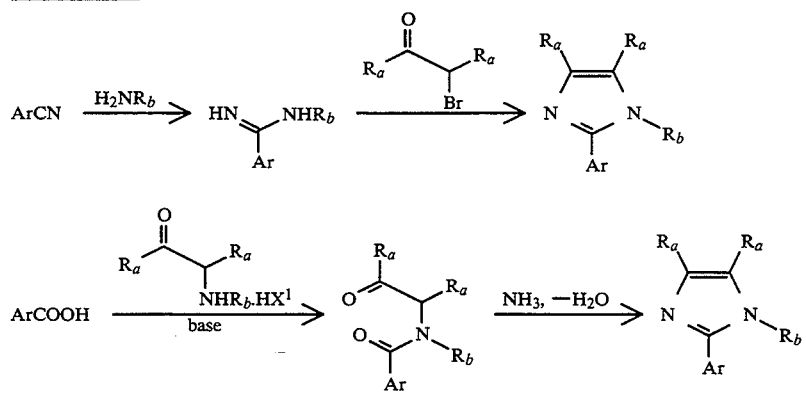
Triazole
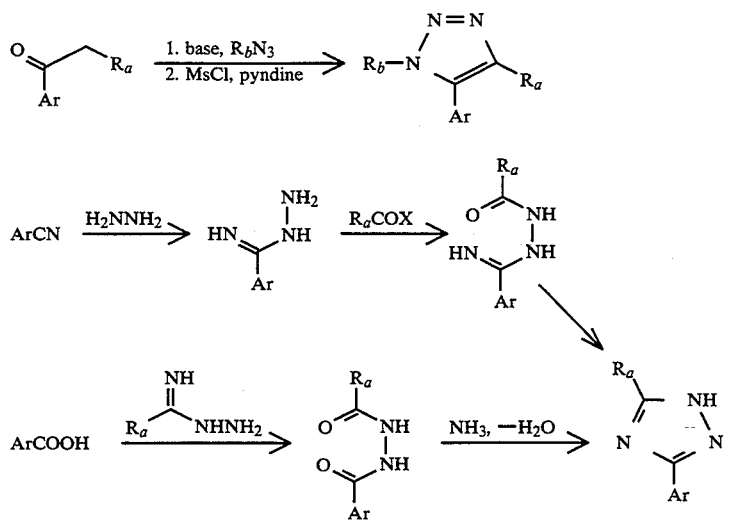
Isoxazole -continued
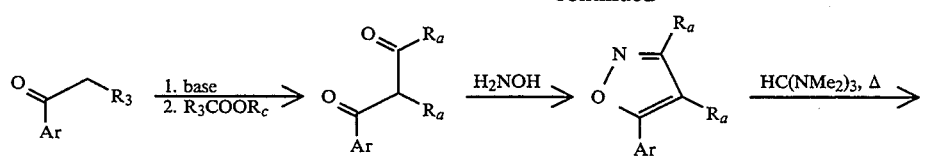
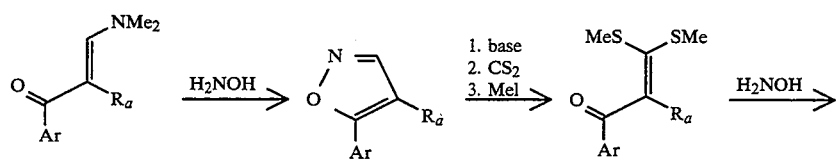
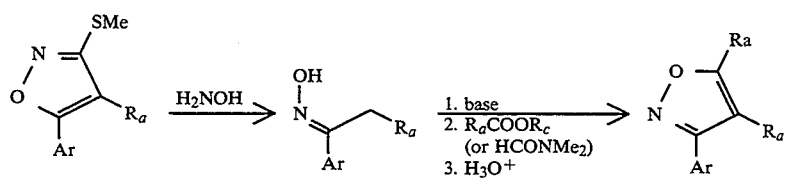
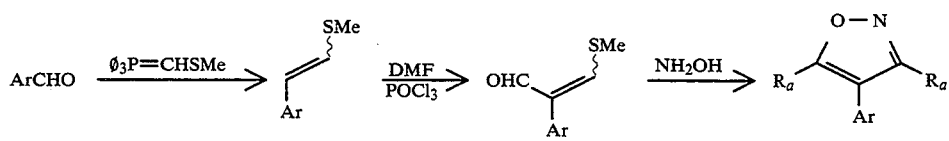
Oxazole (1)
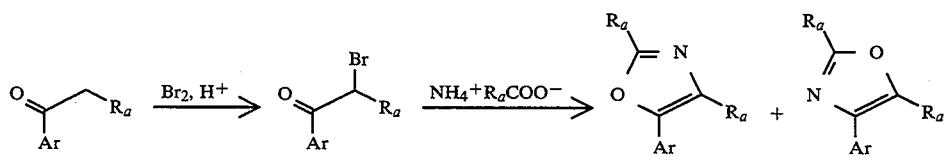
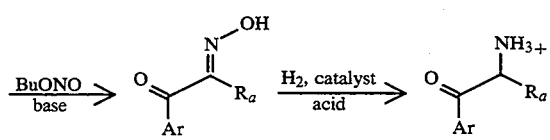
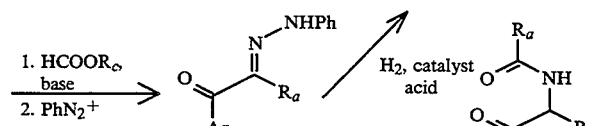
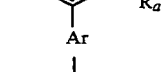
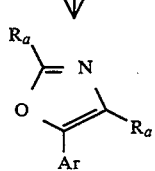
Oxazole (2)

-continued
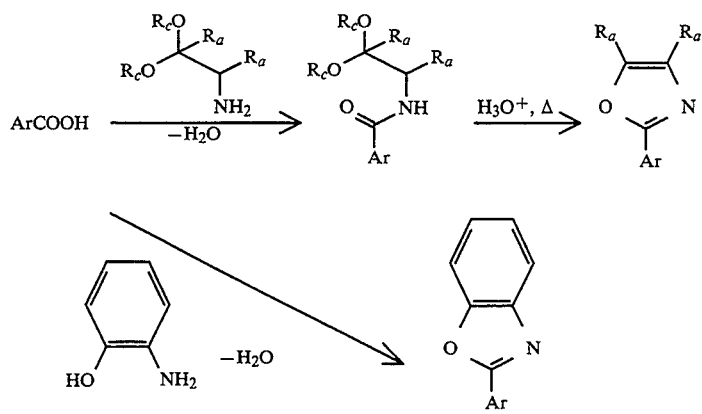
1,2,4- and 1,3,4-Oxadiazole
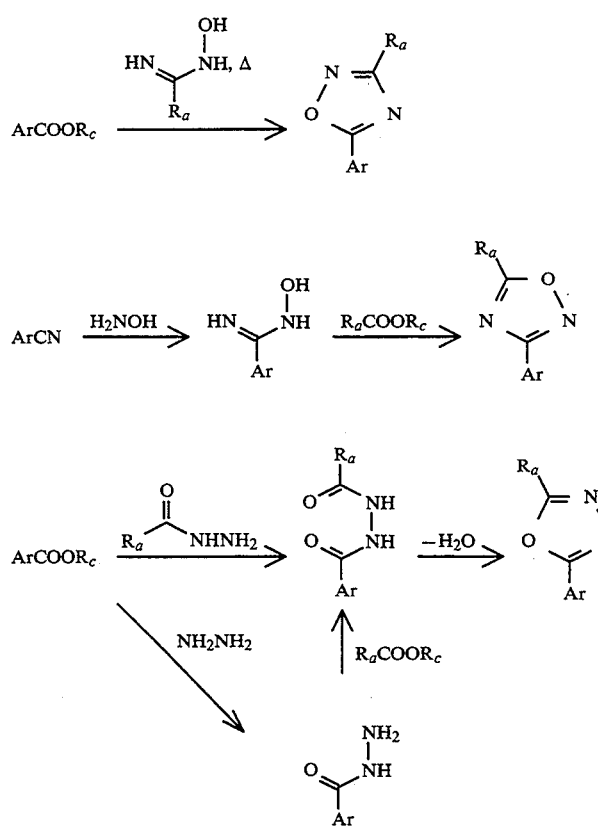
1,2,5-Oxadiazole
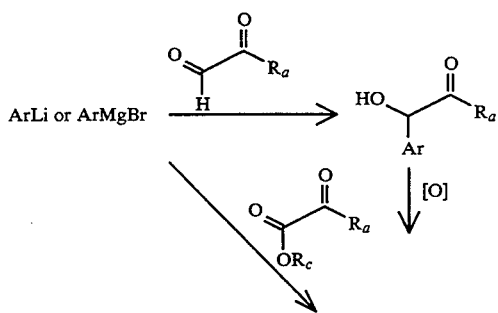

-continued
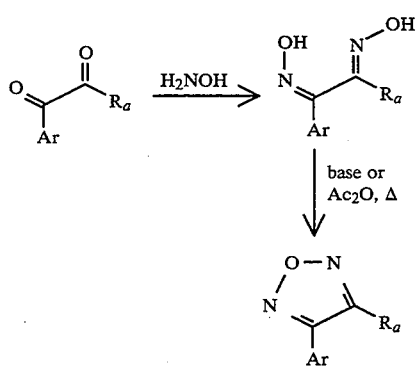
Isothiazole (1)
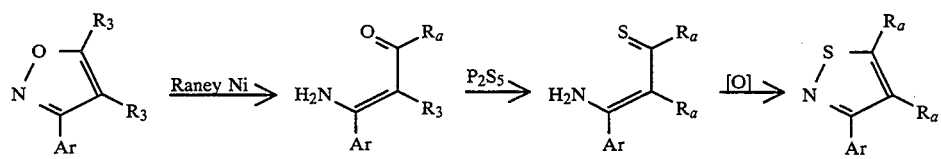
analogous chemistry for 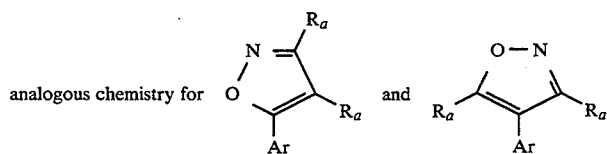
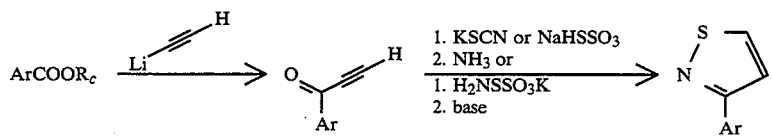
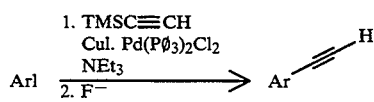
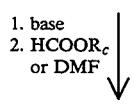
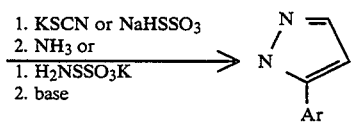
Isothiazole (2)
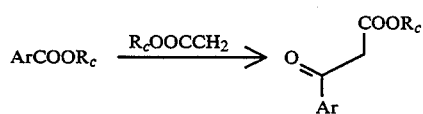
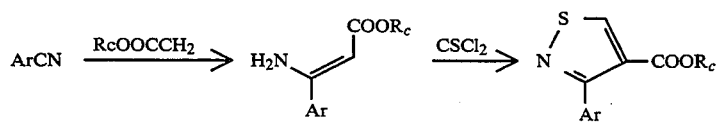

-continued
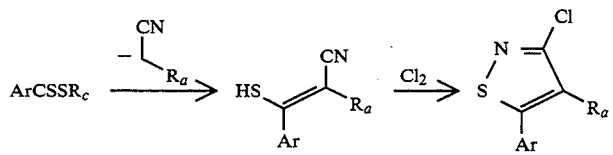
Thiazole (1)
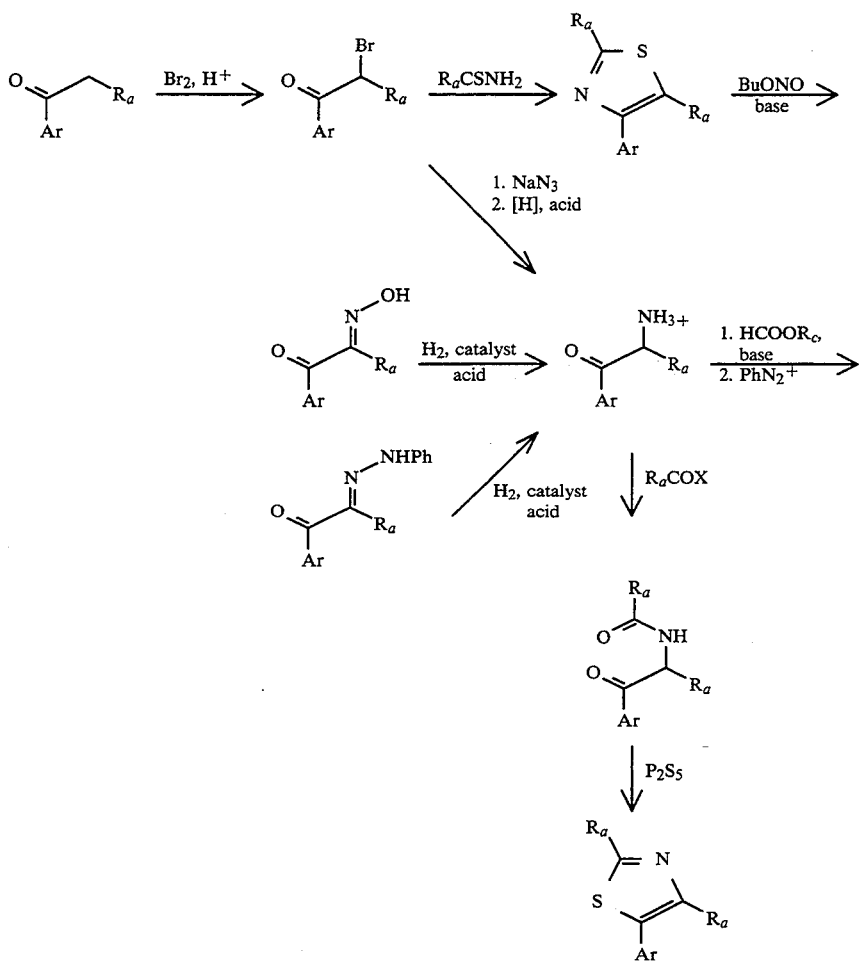
Thiazole (2)
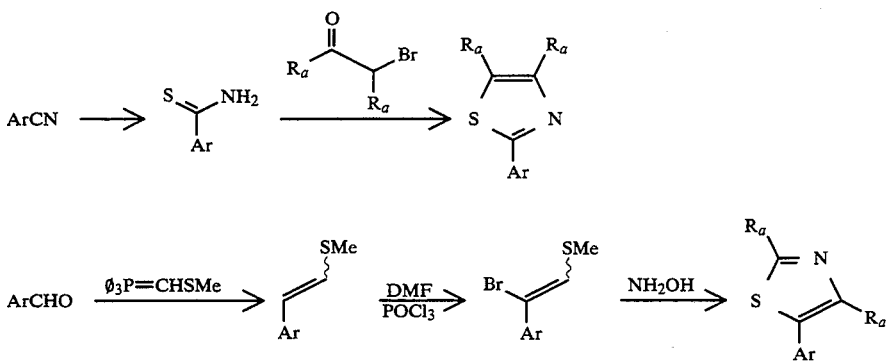
1,2,3- and 1,3,4-Thiadiazole

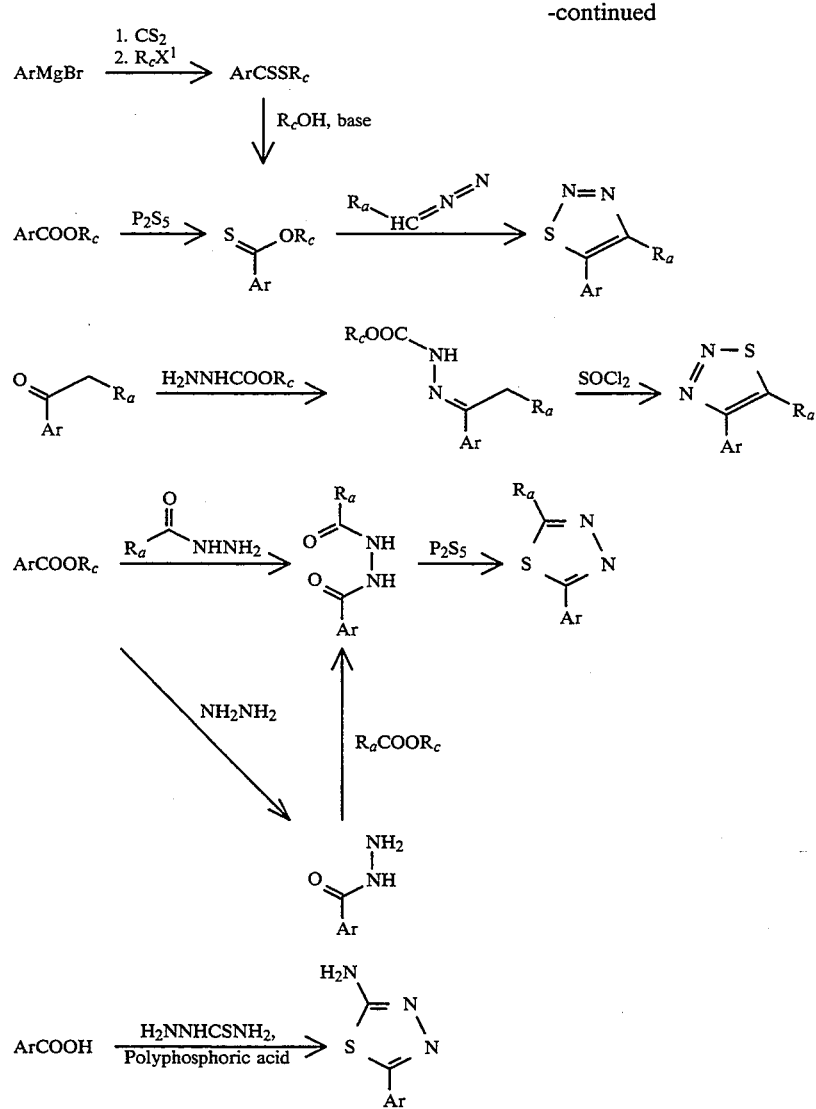
1,2,4- and 1,2,5-Thiadiazole
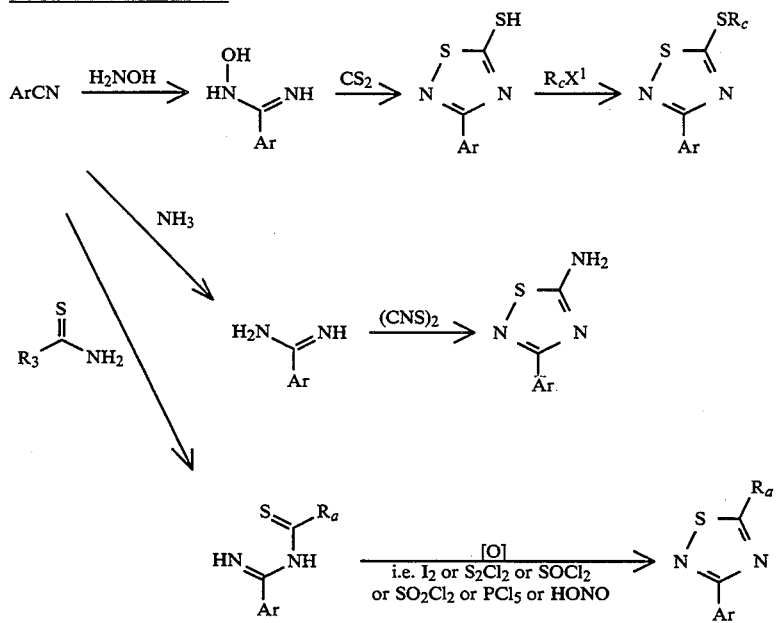

-continued
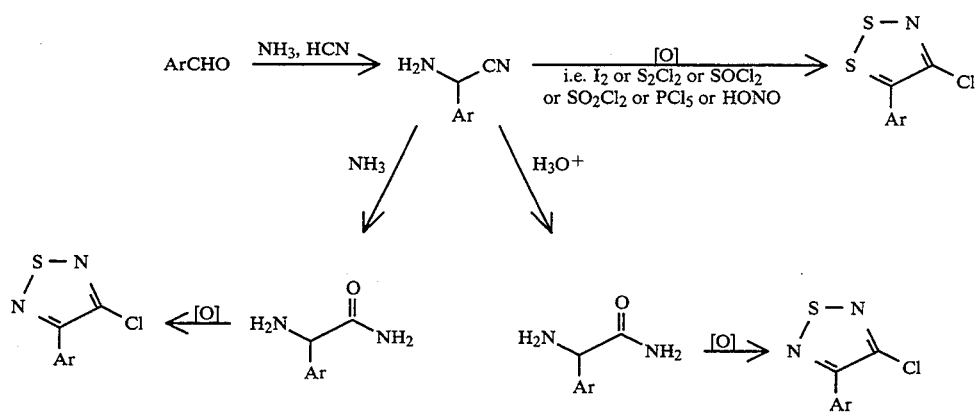
Pyrimidine
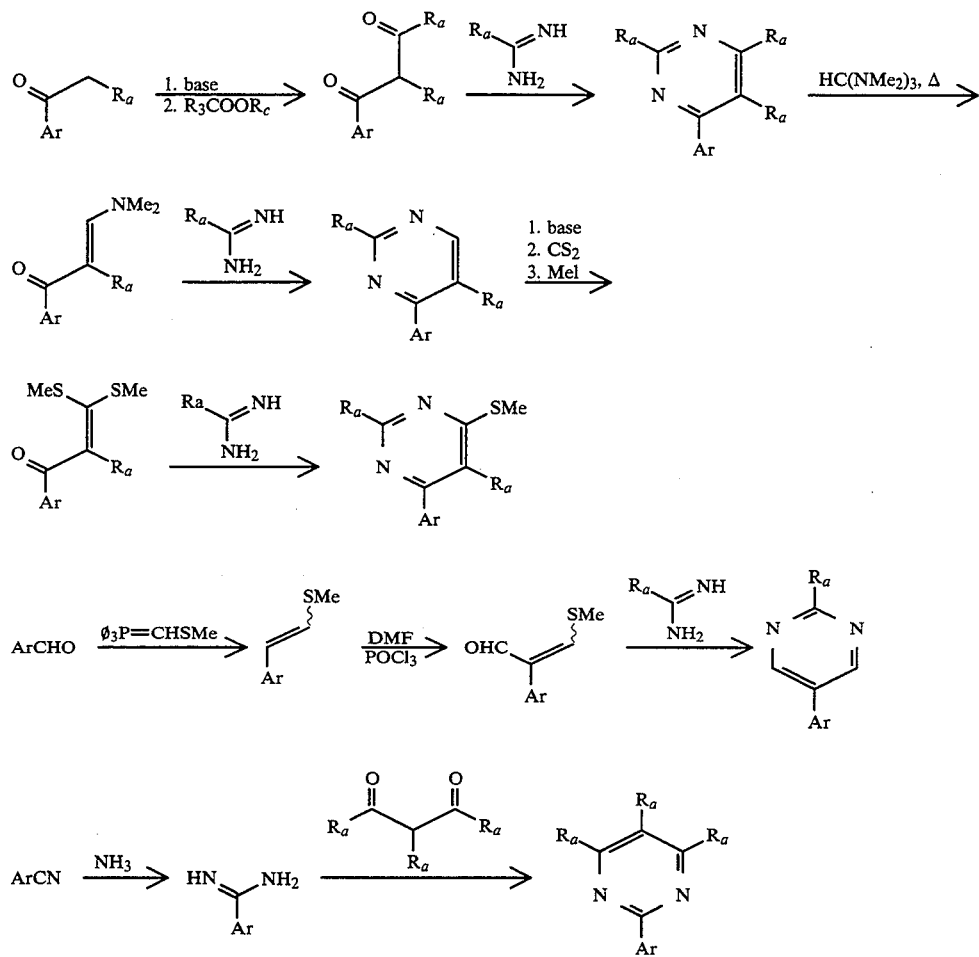
Pyrazine
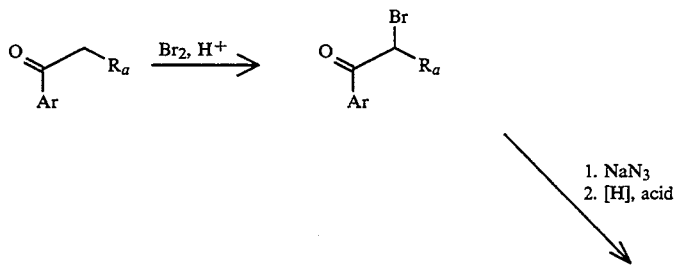
1. NaN₃
2. [H], acid -continued

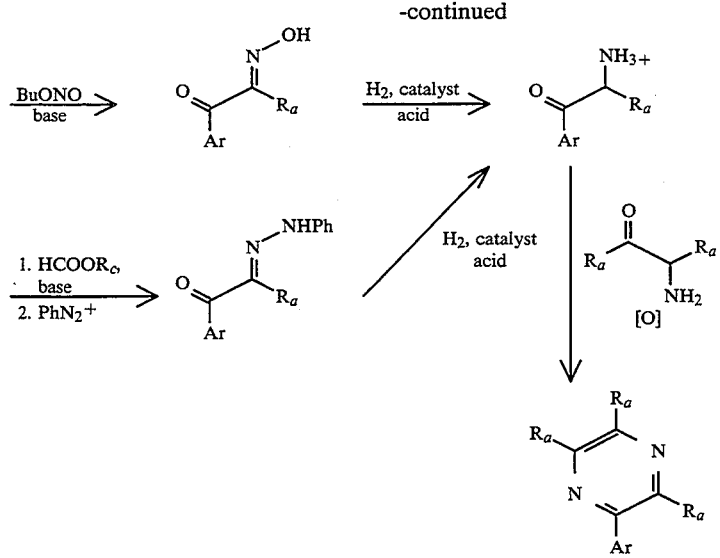

Triazines

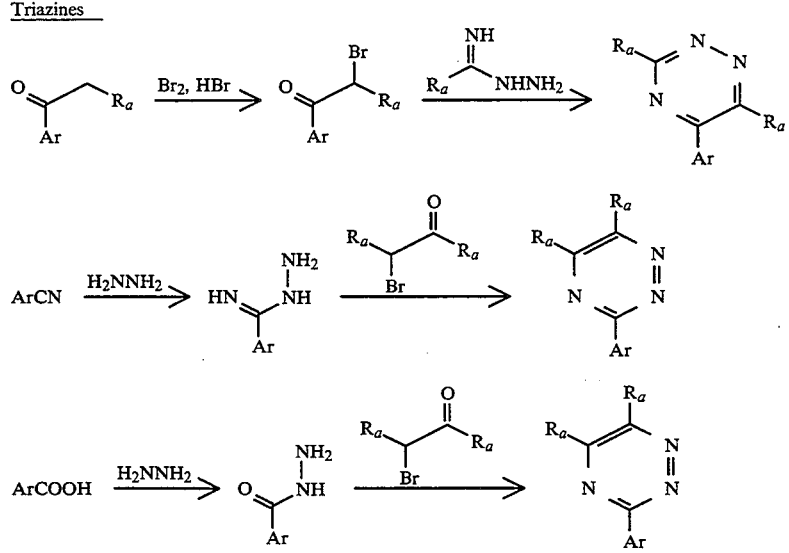

The aforementioned methods of synthesis provide compounds in which the heteroaromatic ring may or may not bear a substituent. The following general reactions provide methodology for incorporating, interconverting, and removing substituents on the heteroaromatic ring. Additional methods for performing these transformations are cited in *Comprehensive Organic Transformations* by Richard C. Larocke, VCH Publishers, Inc., New York (1989). In the following, Ar' refers to the heteroaromatic system attached to the 2-aminotetralin ring system at C-8 or to the 3-aminochromane ring system at C-5.

| A. | Halogen substitutents: | |
|---|---|---|
| | Ar'OH → Ar'X' | POX′$_3$, PX′$_3$, SOX′$_2$, or P(OR)$_3$.X′$_2$ |
| | Ar'NH$_2$ → Ar'X' | 1. HONO; 2. CuX', or KI, or HBF$_4$, Δ |
| B. | O(C$_1$-C$_4$ alkyl): | |
| | Ar'X → Ar'OR' | R'O—, CuI, (DMF, or DMAc, or NMP), Δ |
| | Ar'OH → Ar'OR' | Base, R'X'; or CH$_2$N$_2$ |
| C. | Hydroxy substituent: | |
| | Ar'NH$_2$ → Ar'OH | 1. HONO; 2. H$_3$O+, Δ |
| | Ar'OMe → Ar'OH | 48% HBr, Δ; |

| | | -continued |
|---|---|---|
| | | or BBr$_3$ |
| D. | Cyano substituent: | |
| | Ar'NH$_2$ → Ar'CN | 1. HONO; 2. CuCN |
| | Ar'X' → Ar'CN | CuCN, (DMF, or DMAc, or NMP), Δ or CN—, Δ |
| E. | S(C$_1$-C$_4$ alkyl): | |
| | Ar'NH$_2$ → Ar'SR' | 1. HONO; 2. R'SH, base |
| | Ar'X' → Ar'SR' | R'S—, CuI, (DMF, or DMAc, or NMP), Δ |
| F. | Amino substituent: | |
| | Ar'NO$_2$ → Ar'NH$_2$ | H$_2$, catalyst (i.e. Pt or Pd) |
| G. | Hydrogen substituent: | |
| | Ar'X' → Ar'H | H$_2$, catalyst; or R'$_3$SnH, 2,2'-azobis(2-methyl-propionitrile) Δ |
| | Ar'OH → Ar'H | 1. 5-chloro-1-phenyltetrazole, 2. H$_2$, catalyst |
| | Ar'NH$_2$ → Ar'H | 1. HONO, 2. H$_3$PO$_2$ |
| | Ar'—CH$_2$Ph → Ar'H | H$_2$, catalyst (i.e. Pd) (This applies if the benzyl group is attached to a nitrogen in the heterocyclic ring.) |
| | Ar'SR' → Ar'H | Raney Ni |

The optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents are d- and l-tartaric acids, d- and l-ditoluoyltartaric acids, and the like.

One particularly useful method for producing optically active isomers of the compounds of this invention is via an 8-substituted-2-tetralone or a 5-substituted-3-chromanone. Either of these intermediates may be reductively alkylated with an optically active α-phenethylamine after which the resulting mixture of diastereomers is separated by recognized methodology, such as chromatography. Cleavage of the α-phenethyl moiety produces a correspondingly substituted, optically active 2-amino-1,2,3,4-tetrahydronaphthalene or 3-aminochromane.

The conditions necessary for removing the phenethyl moiety are relatively severe and can tend to disrupt the integrity of the core tetralin or chromane molecule. It has been discovered that the cleavage can be carried out in a much more facile and efficient manner requiring only mild cleavage conditions when the particular α-phenethylamine which is used is p-nitro-α-phenethylamine.

Cleavage of the p-nitro-α-phenethyl moiety is achieved by reduction of the p-nitro group followed by acid-catalyzed solvolysis of the resulting p-amino-α-phenethyl moiety. Reduction of the nitro group can be accomplished by a wide range of reducing agents including, for example, titanium trichloride, lithium aluminum hydride, or zinc/acetic acid, or by catalytic hydrogenation. Solvolytic cleavage takes place when the monohydrochloride (or other monobasic salt) of the reduction product is treated with water or an alcohol at room temperature or, in some instances, at elevated temperatures. A particularly convenient condition for removing the p-nitro-α-phenethyl moiety is hydrogenation of the amine monohydrochloride in methanol over a platinum catalyst.

As indicated hereinabove, compounds highly useful as intermediates to the compounds of this invention are the corresponding 8-bromotetralins. It has been discovered that the 8-bromo compounds in their optically active form are not available using routine methodology whereas they can be prepared using the described method employing p-nitro-α-phenethylamine.

The compounds employed as initial starting materials in the synthesis of the compounds of this invention are well known and readily synthesized by standard procedures commonly employed by those of ordinary skill in the art.

The pharmaceutically acceptable acid addition salts of this invention are typically formed by reacting a 1,2,3,4-tetrahydronaphthalene or chromane of this invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

EXAMPLE 1

Preparation of 2-Di-n-propylamino-8-(1,2,4-oxadiazol-3-yl)-1,2,3,4-tetrahydronaphthalene Sodium (1.4 g, 62.5 mmol) was dissolved in ethanol (100 ml) and hydroxylamine hydrochloride (4.3 g, 62.5 mmol) was added. This mixture was stirred at room temperature for 1 hour and filtered to remove sodium chloride. The filtrate was added to a solution of 2-di-n-propylamino-8-cyano-1,2,3,4-tetrahydronaphthalene (3.2 g, 12.5 mmol) in ethanol (50 ml). The reaction was stirred at 75° for 64 hours, poured into dilute NaOH solution, and extracted with methylene chloride. The extract was dried ($Na_2SO_4$) and concentrated to give 3.5 g of crude product. Purification by flash chromatography using 5% methanol in methylene chloride containing a trace of ammonium hydroxide as the eluting solvent provided 1.37 g of 2-di-n-propylamino-8-(iminohydroximino)-1,2,3,4-tetrahydronaphthalene.

The foregoing product (0.5 g.; 1.7 mmol) was dissolved in 50 ml of THF after which 0.14 ml (1.7 mmol) of pyridine was added. To the mixture then were added 180 mg (2.1 mmol) of the mixed anhydride of acetic acid and formic acid. The mixture was stirred at room temperature for two hours and then was refluxed for one hour. Triethylamine (1 equivalent) and 1.2 equivalents of the mixed anhydride were added. The mixture was stirred at room temperature overnight and then was refluxed for two hours after which it was stirred at room temperature for one week. The mixture was poured into water and extracted with methylene chloride. The extract was dried over sodium sulfate and evaporated to give 480 mg of a residue.

The residue was placed on a silica gel column and was eluted with a mixture of 3% methanol in methylene chloride containing a trace of ammonium hydroxide. The appropriate fractions (Rf=0.7 in 5% methanol in methylene chloride with a trace of ammonium hydroxide) were combined to give 130 mg of the title compound. MS (FD): 300(100)

EXAMPLE 2

Preparation of 2-Di-n-propylamine-8-(5-phenyl-1,2,4-oxadiazol-3-yl)-1,2,3,4-tetrahydronaphthalene, maleate salt 2-Di-n-propylamino-8-(iminohydroximino)-1,2,3,4-tetrahydronaphthalene (290 mg; 1.0 mmol), prepared as in Example 1, dissolved in ethanol was added to ethanol containing sodium ethoxide which had been prepared by adding 30 mg (1.25 mmol) of sodium to the ethanol. The total amount of ethanol in the resulting mixture was 15 ml. Methyl benzoate (1.2 ml; 10.0 mmol) was added, and the mixture was heated to 70° C. for two hours during which time the mixture became slightly cloudy. The mixture was poured into water, and the aqueous mixture then was extracted with methylene chloride. The methylene chloride extract was dried over sodium sulfate and evaporated to give 1.0 g of an oil.

The oil was placed on a silica gel column and was eluted with a 3:1 mixture of hexane and ethyl acetate containing a trace of ammonium hydroxide. The appropriate fractions were combined to give 300 mg of a solid. A portion of the material was converted to the maleate salt and recrystallized from a mixture of ethanol and ether to give 145 mg of the title compound as a white powder, m.p. 101–102° C. Analysis: Theory: C, 68.41; H, 6.77; N, 8.55; Found: C, 68.37; H, 6.44; N, 8.65.

EXAMPLE 3

Preparation of
2-Di-n-propylamino-8-(fur-3-yl)-1,2,3,4-tetrahydronaphthalene

2-Di-n-propylamino-8-bromo-1,2,3,4-tetrahydronaphthalene (1.0 g; 3.2 mmol) was dissolved in 20 ml of THF, and 94 mg (3.9 mmol) of magnesium shavings were added. The mixture was refluxed, and a couple of drops of dibromoethane were added to initiate Grignard formation. The mixture was refluxed for one hour after which it was added to a solution of 0.58 ml (6.4 mmol) of 3-bromofuran and 36 mg (0.03 mmol) of Ni(PPh$_3$)$_4$ in 20 ml of toluene that had been cooled to 0° C. after stirring at room temperature for one hour. The mixture was stirred at room temperature for three hours after which an additional 0.58 ml of 3-bromofuran and 35 mg of Ni(PPh$_3$)$_4$ were added. When the reaction failed to proceed further, 210 mg (0.3 mmol) Ni(PPh$_3$)$_2$Cl$_2$ was added, and the mixture was stirred overnight at room temperature. The mixture then was poured into water and the pH adjusted to 10 with ammonium hydroxide. The mixture was extracted with methylene chloride, dried over sodium sulfate, and evaporated to give 0.8 g of a residue.

The residue was purified twice over a silica gel column using a 4:1 mixture of hexane and ether to obtain 50 mg of pure title compound. MS(FD): 297(100)

EXAMPLE 4

Preparation of
2-Di-n-propylamino-8-(fur-2-yl)-1,2,3,4-tetrahydronaphthalene

Furan (0.3 ml; 3.9 mmol) was dissolved in 10 ml of THF, and the mixture was cooled to −20° C. after which 3.2 ml (3.9 mmols; 1.2M in hexane) of n-butyllithium were added. The mixture was stirred at −20° C. for three hours. The solution was added over a 15 minute period to a refluxing mixture of 1.0 g (3.2 mmol) of 2-di-n-propylamino-8-bromo-1,2,3,4-tetrahydronaphthalene and 190 mg (0.16 mmol) of Pd(PPh$_3$)$_4$ in 50 ml of toluene. The mixture was refluxed for three hours after which analysis by TLC indicated that the reaction was about 30% complete. The mixture was stirred overnight at room temperature, 85 mg of Pd(PPh$_3$)$_4$ were added, and the mixture was heated to reflux. Another 1.2 equivalents of the formed furanyl anion cooled to −78° C., were added slowly to the refluxing reaction mixture. The resulting mixture was refluxed for 3.5 hours after which it was stirred at room temperature overnight. The mixture then was poured into 10% aqueous HCl, and ether was added. The ether layer was separated and extracted twice with 10% HCl. The resulting aqueous layer then was adjusted to pH 12 with ammonium hydroxide and extracted with methylene chloride. The methylene chloride extract was dried over sodium sulfate and evaporated to give 0.74 g of a brown oil.

The oil was placed on a silica gel column and was eluted with a mixture of 1% methanol in methylene chloride containing a trace of ammonium hydroxide. The appropriate fractions were combined to give 160 mg of the title compound. (Rf=0.33 in 2% methanol in methylene chloride containing a trace of ammonium hydroxide)

EXAMPLE 5

2-Di-n-propylamino-8-(1-methylpyrazol-3-yl)-1,2,3,4-tetrahydronaphthalene, maleate salt and 2-Di-n-propylamino-8-(1-methylpyrazol-5-yl)-1,2,3,4-tetrahydronaphthalene, hydrobromide salt A solution of n-butyllithium (1.6M in hexane, 15.1 ml, 24.2 mmol) was added to a solution of 8-bromo-2-di-n-propylamino-1,2,3,4-tetrahydronaphthalene (5.0 g, 16.1 mmol) in THF (50 ml) at −78° and the reaction stirred at −78° for one hour. Gaseous carbon dioxide was bubbled through the reaction at −78° until the deep violet color which forms dissipates. Methyllithium (1.4M in ether, 23 ml) was added. The reaction was stirred at −78° for 30 minutes and warmed to room temperature. The reaction was stirred for an additional ten minutes at room temperature at which time the pink color had been lost. An additional 10 ml of the methyllithium solution was added and the reaction became pink once again. After 15 minutes, the pink color was lost and an additional 10 ml of the methyllithium solution added. The reaction was poured onto ice, made acidic with hydrochloric acid and extracted with ether. The aqueous layer was made basic and extracted with methylenechloride. The basic extracts were dried (Na$_2$SO$_4$) and concentrated to give 3.8 g of crude product. Purification by flash silica gel chromatography using 2:1 hexane:ether containing trace ammonium hydroxide provided 2-di-n-propylamino-8-acetyl-1,2,3,4-tetrahydronaphthalene as a yellow oil (2.7 g, 61%).

2-Di-n-propylamino-8-acetyl-1,2,3,4-tetrahydronaphthalene (3.0 g; 11.0 mmol) was dissolved in 125 ml of toluene after which 4.6 ml (27.5 mmol) of tris(dimethylamino)methane were added. The mixture was heated to 80° C. overnight after which it was evaporated, and the residue was dissolved in 100 ml of methanol. Methylhydrazine (2.9 ml; 54.9 mmol) was added. The mixture was refluxed for six hours and then stirred at room temperature overnight. The mixture was then poured into water, and the aqueous mixture was extracted with methylene chloride. The methylene chloride extract was dried over sodium sulfate and evaporated to give 3.7 g of a residue which contained both of the title compounds.

The residue was placed on a silica gel column and was eluted with a mixture of 2% methanol in methylene chloride containing a trace of ammonium hydroxide. The appropriate fractions were combined to give 2.1 g of the major isomer, 2-di-n-propylamino-8-(1-methylpyrazol-3-yl)-1,2,3,4-tetrahydronaphthalene (Rf=0.31 in 2% methanol in methylene chloride containing a trace of ammonium hydroxide). This material was converted to the maleate salt, and the salt was recrystallized from a mixture of ethanol and ether to give 2.3 g of white crystals, m.p. 139.5°–140.5° C. MS(FD): 311(100) Analysis: Theory: C, 67.42; H, 7.78; N, 9.83; Found: C, 67.62; H, 7.81; N, 9.80.

The appropriate fractions were combined to give 165 mg of the minor isomer, 2-di-n-propylamine-8-(1-methylpyrazol-5-yl)-1,2,3,4-tetrahydronaphthalene. (Rf=0.27 in 2% methanol in methylene chloride containing a trace of ammonium hydroxide) The HBr salt of this material was formed and recrystallized from a mixture of methanol and ethyl acetate to give 30 mg of a solid, m.p. 203°–204° C. MS(FD): 311(100) Analysis: Theory: C, 50.76; H, 6.60; N, 8.88 Found: C, 50.09; H, 6.61; N, 8.65.

EXAMPLE 6

Preparation of 2-Di-n-propylamino-8-(5-hydroxypyrazol-3-yl)-1,2,3,4-tetrahydronaphthalene To a solution of 8-bromo-2-di-n-propylamino-1,2,3,4-tetrahydronaphthalene (1.0 g, 3.22 mmol) in THF (50 ml) at −78° C. was added a solution of n-butyllithium in hexane (1.1M, 4.4 ml, 1.5 eq). The reaction was allowed to stir at −78° for one hour and carbon dioxide gas was bubbled through the reaction. The resulting mixture was warmed to room temperature. After removal of the volatiles from the reaction, the brown oil was poured into $H_2O$ and washed with ether. The organic phase was discarded and the aqueous layer was concentrated and taken up in methanol. HCl gas was bubbled through the solution and the reaction heated to reflux for 3 hours. After cooling, the reaction was poured into $H_2O$ (50 ml), made basic using $NaHCO_3$ (aq), and extracted with ether. The ether extract was dried over $MgSO_4$ and concentrated to give 1 g of a black oil. Purification by flash column chromatography eluting with 4:1 Hex:EtOAc yielded 440 mg of 2-di-n-propylamino-8-(methoxycarboxyl)-1,2,3,4-tetrahydronaphthalene.

A LDA solution was formed from 17 mmol of 2.42 ml diisopropylamine and 17 mmol (17 ml, 1M) nBuli at −78° C. The LDA solution was warmed to −20° C. for 30 minutes and cooled back to −78° C. before adding 2.83 ml (20.96 mmol) of t-butyl acetate. After 10 minutes, 440 mg (1.47 mmol) of 2-di-n-propylamino-8-methoxycarbonyl-1,2,3,4-tetrahydronaphthalene was added in 20 ml of dry THF. This reaction was warmed to room temperature and allowed to stir for 3 days.

The resulting mixture was poured into $H_2O$ (50 ml) and extracted with $CH_2Cl_2$ (3×50 ml). The extract was dried ($MgSO_4$) and concentrated to give 1.8 g of an oil. Purification by flash column chromatography, eluting with 10% methanol in dichloromethane, gave 160 mg of 2-di-n-propylamino-8-(t-butoxycarbonylacetyl)-1,2,3,4-tetrahydronaphthalene as a yellow oil.

Hydrazine (1 ml, 32 mmole) was added to a solution of 500 mg (1.34 mmole) of 2-di-n-propylamino-8-t-butoxycarbonylacetyl-1,2,3,4-tetrahydronaphthalene in 25 ml methanol and stirred at room temperature for for 24 hours. The product was isolated by concentrating the reaction mixture followed by flash chromatography, eluting with 1:1 $CH_2Cl_2$:MeOH, and finally crystallizing from MeOH/EtOAc, m.p. 214°–216° C. Analysis: Theory: C, 72.81, H, 8.68, N, 13.41; Found: C, 73.01, H, 8.81, N, 13.27.

EXAMPLE 7

Preparation of 2-Di-n-propylamino-8-(5-methoxypyrazol-3-yl)-1,2,3,4-tetrahydronaphthalene A solution of 20 mmol diazomethane was prepared by adding 4.29 g (29 mmol) 1-methyl-3-nitro-1-nitrosoguanidine to a 25% solution KOH (10 ml) and $Et_2O$ (30 ml) in an ice bath. The ethereal phase was decanted into a solution of 25 ml methanol containing 400 mg (1.28 mmol) of 2-di-n-propylamino-8-(5-hydroxypyrazol-3-yl)-1,2,3,4-tetrahydronaphthalene. The title compound was isolated by concentrating the reaction and purifying the 500 mg of brown oil crude by flash column chromatography eluting with 9:1 mixture of methylene chloride and methanol. 190 mg were collected. The correct mass of 328 was found using FAB spectrum.

EXAMPLE 8

Preparation of 2-Di-n-propylamino-8-(isoxazol-5-yl)-1,2,3,4-tetrahydronaphthalene, maleic acid salt A solution of 2-di-n-propylamino-8-acetyl-1,2,3,4-tetrahydronaphthalene (0.3 g, 1.1 mmol), prepared as in Example 5, and tris(dimethylamino)methane (0.32 g, 2.2 mmol) in toluene was heated to reflux for 5 hours and at 60° for 18 hours. An additional aliquot of tris(dimethylamino)methane (0.16 g, 1.1. mmol) was added and the reaction stirred at 60° for an additional 2 hours. The reaction was concentrated to give 2-di-n-propylamino-8-(1-oxo-3-(dimethylamino)-prop-2-enyl)-1,2,3,4-tetrahydronaphthalene (0.39 g) as a viscous, orange oil.

Hydroxylamine hydrochloride (0.32 g, 4.6 mmol) was added to a solution of 2-di-n-propylamino-8-(1-oxo-3-(dimethylamino)-prop-2-enyl)-1,2,3,4-tetrahydronaphthalene (0.75 g, 2.29 mmol) in acetic acid (5 ml) and the reaction stirred at room temperature. The reaction was concentrated and the residue dissolved in water. This solution was made basic by the addition of concentrated ammonium hydroxide solution and extracted with ether. The extract was washed with brine, dried with $Na_2SO_4$, and concentrated to give a viscous, light orange oil. The maleate salt was formed. Crystallization from ethanol/ether gave the title compound as off-white crystals (0.24 g). mp 136°–138°. Recrystallization of this salt from ethanol gave colorless crystals (155 mg). m.p. 139°–141° Analysis: Theory: C, 66.65; H, 7.29; N, 6.76; Found: C, 66.86; H, 7.33; N, 6.79.

EXAMPLE 9

Preparation of 2-Di-n-propylamino-8-(thiazol-2-yl)-1,2,3,4-tetrahydronaphthalene, hydrochloride salt Thiazole (0.46 ml; 6.5 mmol) was dissolved in 10 ml of THF, and the mixture was cooled to −78° C. after which n-butyllithium (6.5 mmol; 1.0M in hexane) was added. The mixture was warmed to −20° C., and then was cooled again to −78° C. The resulting mixture was slowly added to a refluxing mixture of 1.0 g (3.2 mmol) of 2-di-n-propylamino-8-bromo-1,2,3,4-tetrahydronaphthalene and 370 mg (0.3 mmol) of $Pd(Ph_3P)_4$ in 50 ml of toluene. An additional 10 ml of THF was added to the mixture in order to achieve complete transfer of the materials to the reaction mixture. Very little, if any reaction was noted. It was felt the anion of the thiazole had either not formed or decomposed. Another two equivalents of thiazole were treated with N-butyllithium in 20 ml of THF at −78° C. for 30 minutes. The resulting mixture, a light yellow slurry, was added to the refluxing reaction mixture, and the mixture was refluxed for 45 minutes and stirred overnight at room temperature. The reaction mixture, now black, was poured into 10% aqueous hydrochloric acid and washed with ether. The aqueous layer was separated, made basic with ammonium hydroxide, and extracted with methylene chloride. The extract was dried over sodium sulfate and evaporated to give 1.6 g of a dark brown oil.

The oil was placed on a silica gel column and was eluted with a gradient of 3:1 to 1:1 hexane and ether containing a trace of ammonium hydroxide. Fractions 12–16 were combined to give 120 mg of a brown oil.

The oil was converted to the hydrobromide salt, and the salt was recrystallized from a mixture of methanol and ethyl acetate to give 45 mg of the title compound as tan crystals. Analysis: Theory: C, 47.91; H, 5.93; N, 5.88; Found: C, 47.62; H, 6.10; N, 6.15.

EXAMPLE 10

Preparation of 2-Di-n-propylamino-8-(2-aminothiazol-4-yl)-1,2,3,4-tetrahydronaphthalene 2-Di-n-propylamino-8-acetyl-1,2,3,4-tetrahydronaphthalene (1.3 g; 4.8 mmol) (prepared as in Example 5) was dissolved in 15 ml of acetic acid, and 1.2 ml (5.7 mmol) of a mixture of 31% hydrogen bromide in acetic acid was added followed by 0.29 ml of bromine in acetic acid. The mixture was stirred at room temperature for 30 minutes after which it was evaporated, and the residue was dissolved in methanol. Thiourea (0.4 g; 5.2 mmol) was added, and the mixture was refluxed for two hours and then stirred at room temperature for two days. The mixture was poured into water, and the pH was adjusted to 12 with ammonium hydroxide. The mixture was then extracted with methylene chloride, and the extract was dried over sodium sulfate and evaporated to give 1.7 g of a residue.

The residue was placed on a silica gel column and was eluted with a 2:1 mixture of ether and hexane containing a trace of ammonium hydroxide. The appropriate fractions were combined to give 0.87 g of the title compound. ($R_f$=0.27 in 3:1 ether and hexane containing a trace of ammonium hydroxide).

The maleate salt was formed. Crystallization from ethanol provided the maleate salt as colorless crystals. m.p. 147°–149° C. Analysis: Theory: C, 55.95; H, 6.43; N, 7.24; Found: C, 56.17; H, 6.23; N, 7.15.

EXAMPLE 11

Preparation of 2-Di-n-propylamino-8-(thiazol-4-yl)-1,2,3,4-tetrahydronaphthalene, p-toluene-sulfonate salt To 5 ml of 85% phosphoric acid was added 0.87 g (2.6 mmol) of 2-di-n-propylamino-8-(2-aminothiazol-4-yl)-1,2,3,4-tetrahydronaphthalene (very little dissolved). The solvent then was altered by addition of 20 ml of 35% sulfuric acid. The mixture was cooled to 0° C., and a concentrated aqueous solution of 460 mg (6.6 mmol) of sodium nitrite was added by syringe under the surface of the reaction mixture. The mixture was added slowly to 20 ml of 50% hypophosphorous acid at 0° C., and the reaction mixture then was warmed to room temperature for one hour. The mixture was poured onto ice and the pH adjusted to 11 with ammonium hydroxide. The mixture was extracted with methylene chloride, and the extract was dried over sodium sulfate and evaporated to give 0.7 g of a residue.

The residue was placed on a silica gel column and was eluted with a 2:1 mixture of hexane and ether containing a trace of ammonium hydroxide. The appropriate fractions were combined to give 350 mg of an oil. This material was converted to the p-toluene sulfonate salt and recrystallized from a mixture of ethyl acetate and hexane to give 220 mg of a tan solid, m.p. 143°–144° C. MS(FD): 315(100) Analysis: Theory(.⅛ $H_2O$): C, 63.38; H, 7.09; N, 5.69; Found: C, 63.29; H, 7.01; N, 5.67.

EXAMPLE 12

Preparation of 2-Di-n-propylamino-8-(quinol-2-yl)-1,2,3,4-tetrahydronaphthalene

2-Di-n-propylamino-8-bromo-1,2,3,4-tetrahydronaphthalene (1 g, 3.22 mmol) was added to a refluxing mixture of magnesium turnings (120 mg, 4.9 mmol) in 50 ml THF. Formation of the Grignard reagent was initiated by addition of 0.2 ml 1,2-dibromoethane (0.002 mmol). After 1.5 hours, 220 mg (0.33 mmol) Ni[PPh$_3$]$_2$Cl$_2$ in 10 ml of THF were added followed by 800 mg (4.89 mmol) of 2-chloroquinoline. The solution continued to reflux for 15 minutes after which it was cooled, poured into water, and extracted three times with methalene chloride. The extract was dried with sodium sulfate and concentrated to obtain 2.1 g of a black oil. The crude was purified by using two flash columns. The first was eluted with 1:1 hexanes:ether and the second with 20:1 methylene chloride:methanol. 130 mg of the title compound were collected as product. Following crystallization in ethanol and water, 66 mg of solid were recovered, m.p. 82° C. Analysis: Theory (.⅛ $H_2O$): C, 82.37; H, 8.48; N, 7.68; Found: C, 82.33; H, 8.44; N, 7.73.

EXAMPLE 13

Preparation of 2-Di-n-propylamino-8-(quinol-3-yl)-1,2,3,4-tetrahydronaphthalene, hydrobromide salt To a refluxing mixture of 520 mg (21 mmol) magnesium in 50 ml THF were added 5 g (16.13 mmol) 2-di-n-propylamino-8-bromo-1,2,3,4-tetrahydronaphthalene. A Grignard reagent was formed after two hours of refluxing and then 1.05 g (1.6 mmol) of Ni[PPh$_3$]$_2$Cl$_2$ in 25 ml of THF was added via syringe. After five minutes, 3-bromoquindine (3 ml; 21 mmol) was added in 25 ml THF. The reaction continued to reflux for one hour.

After cooling, the solution was poured into an aqueous solution of sodium bicarbonate and extracted three times with methylene chloride. After drying with sodium sulfate and concentrating, 7.2 g of a black oil were obtained. This material was purified by flash column chromatography, eluting with a 1:1 mixture of ether:-hexanes.

A portion of the material (500 mg) was used to make HBr salt. Upon crystallization from methanol and ether, 423 mg were recovered, m.p. 200° C. Analysis, for 2HBr salt: Theory: C, 57.71; H, 6.20; N, 5.38; Found: C, 57.75; H, 6.27; N, 5.34.

EXAMPLE 14

Preparation of 2-Di-n-propylamino-8-(pyrid-3-yl)-1,2,3,4-tetrahydronaphthalene, oxalate salt 2-Di-n-propylamino-8-bromo-1,2,3,4-tetrahydronaphthalene (5 g, 16.12 mmol) in 50 ml THF was slowly added to a refluxing mixture of 500 mg (20 mmol) magnesium in 50 ml THF. Initiation of the Grignard reagent was done with a drop of 1,2-dibromoethane added. Reflux continued for two hours before adding 1.05 g (1.6 mmol) Ni(PPh$_3$)$_2$Cl$_2$ in 25 ml THF and 3 ml (31.7 mmol) 3-bromopyridine in 25 ml THF. After refluxing an additional 15 minutes the mixture was cooled, poured into sodium bicarbonate, and extracted with methylene chloride. The extracts were dried with magnesium sulfate and concentrated leaving 10.2 g of black oil.

The crude product was purified with flash column chromatography using 1:1 ether:hexane as solvent to yield 1.05 g of the free base of the title compound.

The oxalic acid salt was formed and crystallized from acetone/ether to give 173 mg of product. m.p. 135° C. Analysis: Theory: C, 69.32; H, 7.59; N, 7.03; Found: C, 68.94; H, 7.62; N, 6.90.

EXAMPLE 15

Preparation of
2-Di-n-propylamino-8-(pyrid-2-yl)-1,2,3,4-tetrahydronaphthalene, oxalate salt 2-Di-n-propylamino-8-bromo-1,2,3,4-tetrahydronaphthalene (5 g, 16.72 mmol) in 50 ml THF was slowly added to a refluxing mixture of 500 mg (20 mmol) magnesium turnings in 50 ml THF. Initiation of the Grignard reagent was made by a drop of 1,2-dibromoethane. Reflux continued for two hours before adding 1.05 g (1.6 mmol) Ni(PPh$_3$)$_2$Cl$_2$ in 25 ml THF and 3 ml (31.7 mmol) 2-bromopyridine in 25 ml THF. The reaction refluxed an additional 15 minutes before cooling pouring into water, and extracting with methylene chloride. The extracts were dried with sodium sulfate and concentrated to yield 10.5 g of a black oil.

Purification was performed by flash column chromatography eluting with 1:1 hexanes:ether to yield 1.5 g of the free base of the title compound. The oxalic acid salt was formed and crystallized from acetone/ether to give 215 mg of a brown powder; m.p. 135° C. Analysis: Theory: C, 69.32; H, 7.59; N, 7.03; Found: C, 69.12; H, 7.64; N, 6.88.

EXAMPLE 16

Preparation of
2-Di-n-propylamino-8-(pyrid-4-yl)-1,2,3,4-tetrahydronaphthalene, oxalate salt 2-Di-n-propylamino-8-bromo-1,2,3,4-tetrahydronaphthalene (5 g; 16.12 mmol) in 50 ml THF was slowly added to a refluxing mixture 500 mg (20 mmol) magnesium turnings in 50 ml THF. Initiation of the Grignard reagent was caused by a drop of 1,2-dibromoethane. Reflux continued for two hours before adding 105 g (1.6 mmol) Ni(PPh$_3$)$_2$Cl$_2$ in 25 ml THF and 3 ml (31.2 mmol) 4-chloropyridine in 25 ml THF. The reaction refluxed an additional 1.5 hours before cooling, pouring into water, and extracting with methylene chloride. The extracts were dried with magnesium sulfate and concentrated to yield 9.7 g of black oil.

Purification was performed by flash column chromatography eluting with 1:1 hexanes:ether. Free base of the title compound (850 mg) was recovered. The oxalic acid salt (206 mg) was made and crystallized in methanol/ether; m.p. 191° C. Analysis: Theory: C, 69.32; H, 7.59; N, 7.03; Found: C, 69.47; H, 7.55; N, 6.99.

EXAMPLE 17

Preparation of
2-Di-n-propylamino-8-(indoxazin-3-yl)-1,2,3,4-tetrahydronaphthalene, hydrochloride salt 2-Di-n-propylamino-8-bromo-1,2,3,4-tetrahydronaphthalene (1.0 g; 3.22 mmol) dissolved in THF (25 ml) was cooled to −78° C., and 2.5 ml of n-butyllithium (1.27M in hexane) were added. After one hour, o-fluorobenzoyl chloride (0.38 ml, 3.22 mmol) was added. The mixture was stirred for 10 minutes at −78° C. after which the reaction was quenched by addition of water at −78° C. The reaction was made basic with NaOH and extracted three times with methylene chloride. The basic extract was dried (Na$_2$SO$_4$) and concentrated to give 2.0 g of crude residue. Purification of this material by flash silica gel chromatography using 1:1 ether:hexane containing a trace of ammonium hydroxide as solvent provided 2-di-n-propylamino-8-(2′-fluorobenzoyl)-1,2,3,4-tetrahydronaphthalene (340 mg).

To 47.5 mg of acetone oxime (0.65 mmol) in 25 ml of THF were added 73 mg (0.65 mmol) of potassium t-butoxide. The mixture was stirred at room temperature for one hour after which 210 mg of 2-di-n-propylamino-8-(2′-fluorobenzoyl)-1,2,3,4-tetrahydronaphthalene in THF were added via a syringe. The resulting mixture was refluxed for three hours after which it was cooled and poured into an aqueous solution of ammonium chloride. The mixture then was extracted with either, and the extract was dried and concentrated to obtain 343 mg of 2-di-n-propylamino-8-[2[(isopropylideneamino)oxy]-benzoyl]-1,2,3,4-tetrahydronaphthalene.

The foregoing compound was stirred at reflux for 2.5 hours in a mixture of 10 ml of 5% hydrochloric acid and 10 ml of ethanol after which it was stirred at room temperature overnight. The mixture then was poured into water, made basic with sodium bicarbonate, and extracted with methylene chloride. The extract was dried over magnesium sulfate and concentrated to obtain 219 mg of impure product.

The residue was purified by flash column chromatography using a 10:1 mixture of methylene chloride and methanol as eluant to obtain 121 mg of the free base of the title compound.

The free base was converted to the hydrochloride salt which was recrystallized from a mixture of ethyl acetate and ether to obtain 65 mg of a solid. m.p. 186° C.

EXAMPLE 18

2-Di-n-propylamino-8-(5-hydroxyisoxazol-3-yl)-1,2,3,4-tetrahydronaphthalene

2-Di-n-propylamino-8-(t-butoxycarbonylacetyl)-1,2,3,4-tetrahydronaphthalene (prepared as in Example 6) (1.0 g, 3.3 mmol) was taken up in 25 ml methanol. Ten equivalents of hydroxylamine hydrochloride (8.3 g, 33 mmol) were added and the reaction stirred at room temperature for 48 hours. The solution was filtered to remove unused hydroxylamine hydrochloride. The mixture was then concentrated and three crystallizations were performed from methanol/ethylacetate. The title compound (30 mg) was recovered.

FD mass spectroscopy shows correct mass of 314.

EXAMPLE 19

Preparation of
2-Di-n-propylamino-8-(5-methoxyisoxazol-3-yl)-1,2,3,4-tetrahydronaphthalene Diazomethane (20 mmol) was generated by adding 4.29 g (29 mmol) 1-methyl-3-nitro-1-nitrosoguanidine to a 25% solution of KOH (10 ml) and ether (30 ml) in an ice bath. The ethereal solution was decanted into a solution of 25 ml methanol containing 200 mg 2-di-n-propylamino-8-(5-hydroxyisoxazol-3-yl)-1,2,3,4-tetrahydronaphthalene. After 15 minutes of stirring, nitrogen gas was blown into the reaction flask to effect removal of the excess diazomethane. The mixture was then poured into water and one gram of crude was recovered after extraction with methylene chloride, drying (magnesium sulfate) and concentration. The crude was purified by flash column chromatography eluting with 10:1 methylene chloride:methanol. The title compound (60 mg) was collected as a brown oil.

EXAMPLE 20

Preparation of 2-Di-n-propylamino-8-(3-bromo-isoxazol-5-yl)-1,2,3,4-tetrahydronaphthalene, maleate salt To a solution of 2-di-n-propylamino-8-iodo-1,2,3,4-tetrahydronaphthalene (4.3 g, 12.1 mmol) in triethylamine (100 ml) was added copper(I) iodide (228 mg), bis(-triphenylphosphine)palladium(II) chloride (841 mg) and trimethylsilylacetylene (1.7 ml). This mixture was stirred at room temperature overnight. The reaction was poured into water and extracted with ether. The extract was washed with brine, dried ($Na_2SO_4$), and concentrated to give 5 g of crude product. Purification by flash chromatography using 20:1 methylene chloride:methanol as solvent gave 4.33 g of 2-di-n-propylamino-8-(2-trimethylsilylethynyl)-1,2,3,4-tetrahydronaphthalene which was used in the next reaction.

A solution of 2-di-n-propylamino-8-(2-trimethylsilylethynyl)-1,2,3,4-tetrahydronaphthalene (4.3 g) and tetraethylammonium fluoride (12.1 mmol) in tetrahydrofuran (150 ml) was stirred at room temperature for 18 hours and at reflux for 6 hours. The reaction was concentrated and the residue dissolved in methylene chloride. This solution was washed with water, dried ($Na_2SO_4$), and concentrated to give 3.6 g of a brown oil. Purification by flash chromatography using 20:1 methylene chloride:methanol as solvent gave 2-di-n-propylamino-8-ethynyl-1,2,3,4-tetrahydronaphthalene (1.1 g, 36% overall).

2-Di-n-propylamino-8-ethynyl-1,2,3,4-tetrahydronaphthalene (900 mg; 3.5 mmol) was stirred at room temperature in 90 ml of ethyl acetate containing 1 ml of water. $Br_2CNOH$ (715.8 mg) in 10 ml of ethyl acetate was added, and the mixture was stirred at room temperature for two days after which 150 mg of potassium carbonate and 250 mg of $Br_2CNOH$ were added. The mixture was stirred for an additional four hours after which it was poured into water and washed with ethyl acetate. The ethyl acetate washes were combined, dried, and concentrated to obtain a residue of 1.0 g. The residue was purified by flash column chromatography using 20:1 $CH_2Cl_2$:MeOH. The appropriate fractions were combined to obtain about 120 mg of material. Ether was added and a solid was formed which was removed by filtration. The filtrate contained product which was converted to the maleate salt. Crystallization from a mixture of ethyl acetate and hexane gave the title compound (84 mg). m.p. 113°–114° C. Analysis: Theory: C, 55.99; H, 5.92; N, 5.68; Found: C, 55.77; H, 5.90; N, 5.48.

EXAMPLE 21

Preparation of 2-Di-n-propylamino-8-(4-methylisoxazol-5-yl)-1,2,3,4-tetrahydronaphthalene, maleate salt 2-Di-n-propylamino-8-bromo-1,2,3,4-tetrahydronaphthalene (8.5 g.; 27.4 mmol) was dissolved in 80 ml of THF and cooled to −78° C. after which 25.7 ml of n-butyllithium (1.6M in hexane) were added. The mixture was stirred at −78° C. for one hour after which 2.4 ml (32.9 mmol) of propionaldehyde were added. The mixture was warmed to room temperature and then poured into water, and extracted with methylene chloride. The extract was dried over sodium sulfate and evaporated to give 9.1 g of a yellow oil.

The oil was placed on a silica gel column and was eluted with a mixture of 3% methanol in methylene chloride containing a trace of ammonium hydroxide. The approriate fractions were combined to give 6.5 g (82.0%) of 2-di-n-propylamino-8-(1'-hydroxypropyl)-1,2,3,-tetrahydronaphthalene as a clear oil.

The foregoing product was dissolved in 250 ml of methylene chloride, and 17.0 g (78.7 mmol) of pyridinium chlorochromate (PCC) were added along with 30 g 4A molecular sieves. The mixture was stirred for three hours at room temperature after which 250 ml of ether and Celite were added. The mixture was poured onto a short silica gel column and eluted with ether. Methanol was added to dissolve the brown sludge which had precipitated upon addition of ether to the reaction. This material was added to the column and eluted with 10% methanol in methylene chloride. The eluent was concentrated to give a brown oil which was further purified by column chromatography employing 2:1 hexanes:ether and then pure ether as solvent. Fractions containing the product were combined and concentrated to give 4.7 g of 2-di-n-propylamino-8-propionyl-1,2,3,4-tetrahydronaphthalene.

2-Di-n-propylamino-8-propionyl-1,2,3,4-tetrahydronaphthalene, (1.5 g; 5.2 mmol) was dissolved in 50 ml toluene, and 2.2 ml of tris(dimethylamino)methane was added. The mixture was heated to 80° C. overnight. The mixture was then evaporated and the residue was taken up in 15 ml of acetic acid. Hydroxylamine hydrochloride (730 mg; 10.4 mmol) was added, and the mixture was stirred at room temperature overnight. The mixture was poured onto water, the pH was adjusted to 11 with ammonium hydroxide, and the resulting mixture was extracted with methylene chloride. The extract was dried over sodium sulfate and evaporated to give 1.5 g of an orange oil.

The oil was placed on a silica gel column and was eluted with a 2:1 mixture of hexane and ether containing a trace of ammonium hydroxide. The appropriate fractions were combined to give 1.0 g (61.3%) of the free base of the title compound.

Fifty mg of the free base were converted to the maleate salt and recrystallized from a mixture of ethanol and ether to give 55 mg of white crystals, m.p. 118° C. Analysis, for $C_{24}H_{32}N_2O_5$: Theory: C, 67.27; H, 7.53; N, 6.54; Found: C, 66.99; H, 7.60; N, 6.35.

EXAMPLE 22

Preparation of 2-Di-n-propylamino-8-(4-ethylisoxazol-5-yl)-1,2,3,4-tetrahydronaphthalene 2-Di-n-propylamino-8-bromo-1,2,3,4-tetrahydronaphthalene (5.0 g; 16.1 mmol) was dissolved in 50 ml of THF, and the mixture was cooled to −78° C. after which 21.0 ml of n-butyllithium (0.92M in hexane) were added. The mixture was stirred for 30 minutes, and 1.85 ml (21.0 mmol) of butyraldehyde were added. The mixture was allowed to warm to room temperature and was stirred overnight after which it was poured into water and extracted with methylene chloride. The extract was dried over sodium sulfate and evaporated to give 6.4 g of a residue. The residue was placed on a silica gel column and was eluted with a mixture of 2% methanol in methylene chloride containing a trace of ammonium hydroxide. The appropriate fractions were combined to give 4.8 g of 2-di-n-propylamino-8-(1'-hydroxybutyl)-1,2,3,4-tetrahydronaphthalene as a thick oil.

The oil (4.0 g; 13.2 mmol) was dissolved in 200 ml of methylene chloride and 4A molecular sieves (30 g) were added. The mixture was stirred, and 10.0 g (46.2 mmol) PCC were added. Stirring was continued for three hours at room temperature after which the mixture was poured onto a pad of silica gel and eluted sequentially with ether and 3% methanol in methylene chloride containing a trace of ammonium hydroxide to recover the product as a brown oil.

The oil was placed on a silica gel column and was eluted with a mixture of 3% methanol and methylene chloride containing a trace of ammonium hydroxide. The appropriate fractions were combined to obtain an oil which, when dissolved in ether, caused a brown precipitate to form. The precipitate was removed by filtration, and the filtrate was evaporated to give 3.0 g of 2-di-n-propylamino-8-butyryl-1,2,3,4-tetrahydronaphthalene as a light brown oil.

Potassium t-butoxide (0.82 g; 7.3 mmol) was suspended in 100 ml of tetrahydrofuran (THF). Ethyl formate (1.0 g; 13.3 mmol) and 2-di-n-propylamino-8-butyryl-1,2,3,4-tetrahydronaphthalene (1.0 g; 3.3 mmol) in THF was added to the mixture. The resulting mixture was stirred at room temperature overnight. Hydroxylamine (1.2 g; 16.6 mmol) was added followed by sufficient water to dissolve the solid. The resulting mixture, having pH 6, was stirred at room temperature for 20 hours after which it was poured into water, and the pH was adjusted to 12 with ammonium hydroxide. The mixture was then extracted with methylene chloride. The extract was dried over sodium sulfate and evaporated. The residue was dissolved in 100 of toluene, and 100 mg of p-toluenesulfonic acid was added. The mixture then was refluxed for 1.5 hours after which it was poured into water and extracted with methylene chloride. The methylene chloride extract was dried over sodium sulfate and evaporated.

The residue was placed on a silica gel column and was eluted with a 2:1 mixture of hexane and ether containing a trace of ammonium hydroxide. The appropriate fractions were combined to give 0.9 g of the title compound. MS(FD): 327(100).

EXAMPLE 23

Preparation of 2-Di-n-propylamino-8-(3-methyl-isoxazol-5-yl)-1,2,3,4-tetrahydronaphthalene, maleate salt Potassium t-butoxide (450 mg; 4.0 mmol) was suspended in THF, and 0.7 ml (7.3 mmol) of ethyl acetate and 0.5 g (1.8 mmol) of 2-di-n-propylamino-8-acetyl-1,2,3,4-tetrahydronaphthalene (prepared as in Example 5) in THF was added. The total amount of THF which was used was 30 ml. The mixture was then stirred overnight at room temperature after which 640 mg (9.2 mmol) of hydroxylamine hydrochloride were added. The reaction mixture was then stirred at room temperature for 64 hours. The mixture was poured into water and the pH adjusted from 6 to 12 with ammonium hydroxide. The mixture then was extracted with a 3:1 mixture of chloroform and isopropyl alcohol. The extract was dried over sodium sulfate and evaporated to give 450 mg of a solid. The solid was dissolved in toluene, a small amount of p-toluenesulfonic acid was added, and the mixture was refluxed for two hours. The mixture then was poured into water, the pH adjusted to 12 with ammonium hydroxide, and the mixture extracted with methylene chloride. The methylene chloride extract was dried over sodium sulfate and evaporated to give 390 mg of a brown oil.

The oil was placed on a silica column and eluted with a mixture of 2% methanol in methylene chloride containing a trace of ammonium hydroxide. The appropriate fractions were combined to give 210 mg (35%) of the free base of the title compound.

The compound was converted to the maleate salt which was recrystallized from a mixture of ethanol and ether to give 200 mg of the title compound, m.p. 125.5°–127.5° C. MS(FD): 313(100). Analysis, for $C_{24}H_{31}N_2O_5$: Theory: C, 67.27; H, 7.53; N, 6.54; Found: C, 67.52; H, 7.29; N, 6.48.

EXAMPLE 24

Preparation of 2-Di-n-propylamino-8-(3-phenylisoxazol-5-yl)-1,2,3,4-tetrahydronaphthalene, hydrobromide salt Acetophenone oxime (750 mg; 5.5 mmol) was dissolved in THF, and the mixture was cooled to −5° C. n-Butyllithium (12.0 ml; 11.1 mmol) was added, and the mixture was stirred at −5° C. for one hour. 2-Di-n-propylamino-8-methoxycarbonyl-1,2,3,4-tetrahydronaphthalene (prepared as in Example 6) (0.8 g; 2.8 mmol) dissolved in THF was added (total THF in the mixture equals 100 ml), and the mixture was warmed to room temperature. The mixture was then poured into water and extracted with methylene chloride. The extract was dried over sodium sulfate, and evaporated to give 1.4 g of a residue.

The residue was placed on a silica gel column and was eluted with a 2:1 mixture of hexane and ether containing a trace of ammonium hydroxide. The appropriate fractions were combined to give 220 mg of the free base of the title compound.

The free base was converted to the hydrobromide salt which was recrystallized from a mixture of methanol and ethyl acetate to give 150 mg of a white powder, m.p. 171.5°–173° C. (MS(FD): 374(100) Analysis, for $C_{25}H_{30}N_2OBr$: Theory: C, 65.93; H, 6.86; N, 6.15; Found: C, 65.74; H, 6.86; N, 5.92.

EXAMPLE 25

Preparation of 2-Di-n-propylamino-8-isoxazol-3-yl)-1,2,3,4-tetrahydronaphthalene, hydrochloride salt To a solution of 2-di-n-propylamino-8-acetyl-1,2,3,4-tetrahydronaphthalene (3.5 mmol) (prepared as in Example 5) in methanol (50 ml) was added a solution of hydroxylamine hydrochloride (2.4 g, 35 mmol) in water (10 ml). The solution was stirred at room temperature overnight. The reaction was poured into water, the pH was adjusted to 12 and then extracted with methylene chloride. The extract was dried ($Na_2SO_4$) and concentrated to give 1.5 g of a thick oil. Purification by flash chromatography using 3% methanol in methylene chloride containing a trace of ammonium hydroxide and then 5% methanol in methylene chloride containing a trace of ammonium hydroxide as eluting solvent provided 0.98 g of 2-di-n-propylamino-8-(1-oximinoethyl)-1,2,3,4-tetrahydronaphthalene.

2-Di-n-propylamino-8-(1-oximidoethyl)-1,2,3,4-tetrahydronaphthalene (0.8 g; 2.8 mmol) was dissolved in THF, and the solution was cooled to −5° C., after which 9.2 ml (9.7 mmol) of n-butyllithium were added. The mixture became deep red. After stirring for one hour at −5° C., N,N-dimethylformamide was added, and the mixture was stirred at room temperature overnight. The mixture was poured into a solution of 3 g of sulfuric acid in 2 ml of a 4:1 mixture of THF and water. The resulting mixture was refluxed for one hour after which it was poured into water and the pH was adjusted to 12 with ammonium hydroxide. The mixture was extracted with methylene chloride, and the extract was dried over sodium sulfate and evaporated to give 1.1 g of a residue.

The residue was placed on a silica gel column and was eluted with a 2:1 mixture of hexane and ether containing a trace of ammonium hydroxide. The appropriate fractions were combined to give 210 mg of the free base of the title compound.

The free base was converted to the hydrochloride salt and recrystallized twice from a mixture of methanol and ethyl acetate to give 100 mg of a tan crystalline solid, m.p. 183°–84° C. Analysis: Theory: C, 68.14; H, 8.13; N, 8.37; Found: C, 67.74; H, 8.30; N, 8.20.

EXAMPLE 26

Preparation of
2-Di-n-propylamino-8-(4-methylisoxazol-3-yl)-1,2,3,4-tetrahydronaphthalene, hydrobromide salt To a solution of 2-di-n-propylamino-8-propionyl-1,2,3,4-tetrahydronaphthalene (0.7 g, 2.4 mmol) (prepared as in Example 21) in methanol (40 ml) was added a solution of hydroxylamine hydrochloride (1.7 g, 24 mmol) in water (10 ml). The solution was stirred at room temperature overnight. The reaction was poured into water, the pH was adjusted to 12 and then extracted with methylene chloride. The extract was dried ($Na_2SO_4$) and concentrated to give 760 mg of crude 2-di-n-propylamino-8-(1-oximinopropyl)-1,2,3,4-tetrahydronaphthalene sufficiently pure to be used in the next step.

2-Di-n-propylamino-8-(1-oximido-propyl)-1,2,3,4-tetrahydronaphthalene (0.76 g; 2.5 mmol) was dissolved in THF, and the solution was cooled to −5° C. after which 8.8 ml (8.8 mmol) of n-butyllithium were added. The mixture was stirred for one hour at −5° C. during which time the mixture became deep orange-red. DMF (0.39 ml; 5.0 mmol) was added, and cooling was discontinued. The mixture was stirred for 45 minutes and then poured into a mixture containing 3 g of sulfuric acid in 25 ml of a 4:1 mixture of THF and water. The resulting mixture was refluxed for one hour and then stirred at room temperature overnight. The mixture was poured into water, washed with ether, and the pH adjusted to 12 with ammonium hydroxide solution. The mixture was then extracted with methylene chloride, and the extract was dried over sodium sulfate and evaporated to a residue (1.0 g).

The residue was placed on a silica gel column and was eluted with a 2:1 mixture of hexane and ether containing a trace of ammonium hydroxide. The appropriate fractions were combined to give 340 mg of the free base of the title compound.

The free base was converted to hydrobromide salt, recrystallized from a mixture of methanol and ethyl acetate to give 215 mg of the title compound, m.p. 156°–157° C. MS(FD): 313(100). Analysis: Theory: C, 61.07; H, 7.43; N, 7.12; Found: C, 61.06; H, 7.71; N, 6.72.

EXAMPLE 27

Preparation of
2-Di-n-propylamino-8-(4-ethylisoxazol-3-yl)-1,2,3,4-tetrahydronaphthalene 2-Di-n-propylamino-8-butyryl-1,2,3,4-tetrahydronaphthalene (1 g; 3.3 mmol) (prepared as in Example 22) was dissolved in 40 ml of methanol, and 2.3 g (33 mmol) of hydroxylamine hydrochloride dissolved in water were added. The mixture was stirred at room temperature for 20 hours after which it was poured into water, and the pH was adjusted to 10 using ammonium hydroxide. The mixture then was extracted with methylene chloride, and the extract was dried over sodium sulfate and evaporated. The residue was placed on a silica gel column and was eluted with a gradient mixture of 3–5% methanol in methylene chloride containing a trace of ammonium hydroxide. The appropriate fractions were combined and evaporated to give 1.1 g of 2-di-n-propylamino-8-(1-oximino-butyl)-1,2,3,4-tetrahydronaphthalene. (Rf=0.30 in 4% methanol and methylene chloride containing a trace of ammonium hydroxide) MS(FD): 316(100).

The product (1.0 g; 3.2 mmol) was dissolved in THF, and 5.0 ml (7.0 mmol) of n-butyllithium were added. The mixture was stirred at −5° C. for one hour during which a red color developed. N,N-Dimethylformamide (0.5 ml; 6.3 mmol) was added, and the mixture was stirred at room temperature overnight. The mixture then was poured into 40 ml of a 4:1 mixture of THF and water containing 6 g of sulfuric acid. The resulting mixture was refluxed for two hours, cooled to room temperature, poured into water, and the pH was adjusted to 12 using ammonium hydroxide. The mixture then was extracted with methylene chloride, and the extract was dried over sodium sulfate and evaporated to give 1.15 g of a residue.

The residue was placed on a silica gel column and was eluted with a 2:1 mixture of hexane and ether containing a trace of ammonium hydroxide. The appropriate fractions were combined to give 270 mg of the title compound. (Rf=0.28 in 2:1 hexane and ether containing a trace of ammonium hydroxide) MS(FD): 327(100).

EXAMPLE 28

Preparation of
2-Di-n-propylamino-8-(5-methylisoxazol-3-yl)-1,2,3,4-tetrahydronaphthalene, hydrobromide salt 2-Di-n-propylamino-8-(1-oximidoethyl)-1,2,3,4-tetrahydronaphthalene (prepared as in Example 25) (1.1 g; 3.8 mmol) was dissolved in 100 ml of THF and cooled to −5° C. n-Butyllithium (5.3 ml; 8.4 mmol) was added, and a deep red color persisted. After thirty minutes, 0.45 ml (4.6 mmol) of ethyl acetate was added, and the mixture was warmed to room temperature. The mixture then was poured into water and the total extracted with methylene chloride. The extract was dried over sodium sulfate and evaporated to a residue. The residue was dissolved in toluene, and 100 mg of p-toluenesulfonic acid were added. The mixture was refluxed for one hour after which it was cooled to room temperature, poured into water, and the pH adjusted to 12 with ammonium hydroxide. The mixture was extracted with methylene chloride, and the extract was dried over sodium sulfate and evaporated to give 1.1 g of a residue.

The residue was placed on a silica gel column and was eluted first with a 2:1 mixture of hexane:ether containing a trace of ammonium hydroxide and then a 1:1 mixture of hexane and ether containing a trace of ammonium hydroxide. The appropriate fractions were combined to give 260 mg of the free base which was converted to the hydrobromide salt. The salt was recrystallized from ethyl acetate to give 115 mg of dark crystals which were crystallized from a mixture of methanol, ethyl acetate, and hexane to give 100 mg of the title compound, m.p. 165°–165.5° C. MS(FD): 312(100). Analysis: Theory: C, 61.07; H, 7.43; N, 7.12; Found: C, 61.30; H, 7.43; N, 6.92.

EXAMPLE 29

Preparation of
2-Di-n-propylamino-8-(5-methylthioisoxazol-3-yl)-1,2,3,4-tetrahydronaphthalene 2-Di-n-propylamino-8-acetyl-1,2,3,4-tetrahydronaphthalene (prepared as in Example 5) (1.0 g; 3.7 mmol) dissolved in THF was added to a solution of 0.9 g (8.1 mmol) of potassium t-butoxide in THF. The mixture was stirred at room temperature for one hour. Carbon disulfide (0.26 ml, 4.4 mmol) was added, and the mixture was stirred for thirty minutes after which 0.52 ml (8.4 mmol) of methyl iodide was added. Stirring was continued overnight after which the mixture was poured into water, the pH adjusted to 12 using ammonium hydroxide, and the resulting mixture extracted with methylene chloride. The extract was dried over sodium sulfate and evaporated to give 1.5 g of a yellow oil.

The oil was placed on a silica gel column and was eluted with a mixture of 3% methanol in methylene chloride containing a trace of ammonium hydroxide. 2-Di-n-propylamino-8-[3,3-di(methylthio)-1-oxo-prop-2-en-1-yl]-1,2,3,4-tetrahydronaphthalene (1.1 g) was obtained.

The foregoing product (0.36 g; 0.95 mmol) and 260 mg (3.8 mmol) of hydroxylamine hydrochloride in 10 ml of methanol was added to a sodium methoxide solution prepared by adding 130 mg (5.7 mmol) of sodium to 10 ml of methanol. The mixture was refluxed overnight after which it was cooled to room temperature, poured into water, and the pH adjusted to 12 using a dilute solution of hydrochloric acid. The mixture then was extracted with methylene chloride and a 3:1 mixture of chloroform and isopropyl alcohol. The extract was dried over sodium sulfate and evaporated to give 180 mg of a residue.

The residue was separated on a flash silica gel column using a gradient of 3–5% methanol in methylene chloride containing a trace of ammonium hydroxide. The appropriate fractions were combined to give 90 mg (27.4%) of the title compound. (Rf=0.39 in 3% methanol and methylene chloride containing a trace of ammonium hydroxide) MS(FD): 344(100).

EXAMPLE 30

Preparation of
2-Di-n-propylamino-8-(3-methylthioisoxazol-5-yl)-1,2,3,4-tetrahydronaphthalene, maleate salt 2-Di-n-propylamino-8-[3,3-di(methylthio)-1-oxo-prop-2-en-1-yl]-1,2,3,4-tetrahydronaphthalene (prepared as in Example 29) (0.64; 1.7 mmol) was dissolved in a mixture of toluene and acetic acid. Hydroxylamine hydrochloride (1.2 g; 17 mmol) and sodium acetate (1.2 g; 14 mmol) in 10 ml of water were added. Ethanol (10 ml) then was added to render the mixture homogeneous. The mixture was heated to 100° C. for 18 hours after which 0.6 g of hydroxylamine hydrochloride was added. The mixture was stirred at 100° C. for an additional four hours, and another 0.6 g of hydroxylamine hydrochloride was added. The mixture then was stirred for two hours at 100° C. and then at room temperature overnight. The mixture was poured into water, and the aqueous mixture was washed twice with ether and then extracted with 10% hydrochloric acid. The aqueous layers were combined and made basic (pH 12). The mixture was then extracted with methylene chloride, and the extract was dried over sodium sulfate and evaporated to give 560 mg of a dark yellow oil.

The oil was placed on a silica gel column and was eluted with a gradient of 1.5–2% methanol in methylene chloride containing a trace of ammonium hydroxide. The appropriate fractions were combined to give 230 mg of product. The product was converted to the maleate salt and recrystallized from a mixture of ethyl acetate and hexane to give 210 mg of the title compound, m.p. 118°–119.5° C. MS(FD): 344(100). Analysis: Theory: C, 62.59; H, 7.00; N, 6.08; Found: C, 62.84; H, 7.04; N, 6.02.

EXAMPLE 31

Preparation of
2-Di-n-propylamino-8-(4-methoxyisoxazol-5-yl)-1,2,3,4-tetrahydronaphthalene hydrobromide 2-Di-n-propylamino-8-bromo-1,2,3,4-tetrahydronaphthalene (5.0 g; 16.1 mmole) was dissolved in 25 ml of THF and cooled to −78° C. after which 3.22 ml of n-butyllithium (1M in hexane) was added. The mixture was maintained at −78° C. for 1.5 hours. This solution was transferred via cannula to a solution of methyl methoxyacetate (7.5 ml, 160 mmol) in THF at −78° C. The reaction mixture was stirred at room temperature overnight, poured into NaHCO3 solution and extracted with CH2Cl2. The extract was dried (Na2SO4) and concentrated to give 6.8 g of crude product.

The material then was placed on a chromatographic column, and the product was eluted using 4% methanol in methylene chloride containing a trace of ammonium hydroxide. The appropriate fractions were combined to give 1.4 g of 2-di-n-propylamino-8-methoxyacetyl-1,2,3,4-tetrahydronaphthalene.

A solution of 2-di-n-propylamino-8-methoxyacetyl-1,2,3,4-tetrahydronaphthalene (1.0 g) and tris(dimethylamino)methane (1.5 ml) in toluene (25 ml) was heated to reflux for 1.5 hours. The reaction was concentrated to give crude 2-di-n-propylamino-8-(1-oxo-2-methoxy-3-(dimethylamino)-prop-2-enyl)-1,2,3,4-tetrahydronaphthalene (1.2 g).

Hydroxylamine hydrochloride (1.2 g) was added to a solution of 2-di-n-propylamino-8-(1-oxo-2-methoxy-3-(dimethylamino)-prop-2-enyl)-1,2,3,4-tetrahydronaphthalene (1.1 g) in methanol and the reaction stirred at room temperature overnight. The reaction was concentrated and the residue dissolved in toluene. p-Toluenesulfonic acid (660 mg) was added to the solution and the reaction heated to reflux for 2 hours. The reaction was concentrated and the residue dissolved in a mixture of water and methylene chloride. This mixture was poured into a sodium bicarbonate solution and the resulting mixture extracted with methylene chloride. The extract was dried with MgSO4 and concentrated to give an oil (600 mg). Purification by flash chromatography using 1:1 ether:hexanes as solvent provided 160 mg of the free base of the title compound. The hydrobromide salt was formed. Two recrystallizations from methanol/ether gave the title compound as white crystals (86 mg). m.p. 178° C. Analysis: Theory: C, 58.68; H, 7.14; N, 6.84; Found: C, 58.88; H, 7.23; N, 6.60

EXAMPLE 32

Preparation of
2-Di-n-propylamino-8-(2-aminopyrimidin-4-yl)-1,2,3,4-tetrahydronaphthalene 2-Di-n-propylamino-8-(1-oxo-3-(dimethylamino)-prop-2-enyl)-1,2,3,4-tetrahydronaphthalene, prepared as in Example 8 (0.18 g; 0.55 mmol) was dissolved in 3 ml of ethanol. To the mixture was added 0.07 g (1.1 mmol) of guanidine, and the mixture was stirred at 60° C. under nitrogen for 18 hours. The mixture then was cooled to room temperature during which a crystalline solid formed. The crystals were filtered, washed with isopropyl alcohol, ether, and dried in vacuo to give 70 mg of the title compound as glistening plates. The product was recrystallized from isopropyl alcohol to obtain colorless crystals, m.p. 188°–189° C. Analysis: Theory: C, 74.04; H, 8.70; N, 17.27; Found: C, 74.30; H, 8.70; N, 17.45.

EXAMPLE 33

Preparation of
2-Di-n-propylamino-8-(pyrazol-3-yl)-1,2,3,4-tetrahydronaphthalene oxalate salt 2-Di-n-propylamino-8-(1-oxo-3-(dimethylamino)-prop-2-enyl)-1,2,3,4-tetrahydronaphthalene, prepared as in Example 8 (0.75 g; 2.29 mmol) was dissolved in 10 ml of methanol. To the mixture was added 0.16 ml of hydrazine, and the mixture was stirred at room temperature under nitrogen for 18 hours after which the volatiles were removed in vacuo to obtain a dark orange residue. The residue was dissolved in ether and placed on a flash silica column. The column was eluted with ether containing a trace of ammonium hydroxide.

Fractions 9–13 were collected, combined and concentrated in vacuo to give 0.39 g of a colorless viscous oil. The oil was converted to the oxalate salt which was crystallized from a mixture of ethanol and ether to obtain 0.26 g of the title compound as colorless crystals, m.p. 148°–150° C. Analysis: Theory: C, 65.10; H, 7.54; N, 10.84; Found: C, 65.33; H, 7.44; N, 10.83.

EXAMPLE 34

Preparation of
2-Di-n-propylamino-8-(3-phenyl-1,2,4-oxadiazol-5-yl)-1,2,3,4-tetrahydronaphthalene maleate salt Sodium (0.046 g; 2 mmol) was added to 20 ml of absolute ethanol. To the resulting solution then were added 1.63 g (12 mmol) of benzamide oxime followed by 0.56 g (2 mmol) of 2-di-n-propylamino-8-methoxycarbonyl-1,2,3,4-tetrahydronaphthalene. The mixture was stirred at reflux for 18 hours after which it was filtered, and the filtrate was diluted with water. The aqueous mixture was extracted with methylene chloride, and the organic portion was combined, dried over sodium sulfate, and concentrated in vacuo to give a green oil.

The oil, dissolved in methylene chloride, was placed on a flash silica column, and the column was eluted with a 1:1 mixture of hexanes and ether containing a trace of ammonium hydroxide.

Fractions 4–7 were combined and concentrated in vacuo to give 0.44 g of a colorless oil. The product was converted to the maleate salt and crystallized from a mixture of ethanol and ether at room temperature to give 0.28 g of the title compound as colorless crystals, m.p. 144°–145° C. Analysis: Theory: C, 68.41; H, 6.77; N, 8.55; Found: C, 68.65; H, 6.64; N, 8.55.

EXAMPLE 35

Preparation of
2-Di-n-propylamino-8-(3-methyl-1,2,4-oxidiazol-5-yl)-1,2,3,4-tetrahydronaphthalene maleate salt Sodium (0.023 g; 1 mmol) was added to 10 ml of absolute ethanol. To the mixture then were added 0.44 g (6 mmol) of acetamide oxime followed by 0.29 g (1 mmol) of 2-di-n-propylamino-8-methoxycarbonyl-1,2,3,4-tetrahydronaphthalene. The mixture was stirred at reflux for hours after which it was cooled to room temperature and diluted with water. The aqueous mixture then was extracted with methylene chloride, the organics were combined, dried over sodium sulfate, and concentrated in vacuo to give 0.39 g of a light yellow oil.

The oil was dissolved in hexanes and placed on a flash silica column. The column was eluted with a 1:1 mixture of hexanes and ether containing a trace of ammonium hydroxide.

Fractions 6–9 were combined and concentrated in vacuo to give 0.28 g of a colorless, viscous oil. The maleate salt was formed and recrystallized from ethanol:ether to give 110 mg of colorless crystals, m.p. 115°–117° C. Analysis: Theory: C, 64.32; H, 7.28; N, 9.78; Found: C, 64.29; H, 7.15; N, 9.68.

As noted above, the compounds of this invention have binding affinity for the 5-HT$_{1a}$ receptor. Therefore, another embodiment of the present invention is a method of modulating the activity of the 5-HT$_{1a}$ receptors which comprises administering to a mammal in need thereof a pharmaceutically effective amount of a compound of the invention.

The term "pharmaceutically effective amount", as used herein, represents an amount of a compound of the invention which is capable of binding to serotonin 1a receptors. The specific dose of compound administered according to this invention will, of course, be determined by the particular circumstances surrounding the case, including, for example, the compound administered, the route of administration, and the condition being treated. A typical daily dose generally will contain from about 0.01 mg/kg to about 20 mg/kg of the active compound of this invention. Preferred daily doses generally will be from about 0.05 to about 10 mg/kg, and ideally from about 0.1 to about 5 mg/kg.

The compounds can be administered by a variety of routes including oral, rectal, transdermal, subcutaneous, intravenous, intramuscular, and intranasal.

A variety of physiologic functions have been shown to be subject to influence by brain serotonergic neural systems. As such, the compounds of this invention are believed to have the ability to treat in mammals a variety of 5-HT mediated states and disorders such as sexual disorders, eating disorders, depression, alcoholism, pain, senile dementia, anxiety, gastrointestinal disorders, hypertension, and smoking. Therefore, the present invention also provides methods of treating the above disorders at rates set forth above for action in mammals at 5-HT receptors.

The following experiment was conducted to demonstrate the ability of compounds of the present invention to bind to serotonin 1a receptors. Sites specifically labeled by tritiated 8-hydroxy-2-dipropylamino-1,2,3,4-tetrahydronaphthalene ($^3$H-8-OH-DPAT) have been identified as 5-HT$_{1A}$ receptors. This general procedure is set forth in Wong et al., *J. Neural Transm.* 71:207–218 (1988).

Male Sprague-Dawley rats (110–150 g) from Harlan Industries (Cumberland, Ind.) were fed a Purina Chow ad libitum for at least 3 days before being used in the studies. Rats were killed by decapitation. The brains were rapidly removed, and the cerebral cortices were dissected out at 4° C.

Brain tissues were homogenized in 0.32M sucrose. After centrifugation at 1000×g for 10 min and then at 17000×g for 20 min, a crude synaptosomal fraction was sedimented. The pellet was suspended in 100 vol of 50 mM Tris-HCl, pH 7.4, incubated at 37° C. for 10 min, and centrifuged at 50000×g for 10 min. The process was repeated and the final pellet was suspended in ice-chilled 50 mM Tris-HCl, pH 7.4.

Binding of $^3$H-8-OH-DPAT was performed according to the previously described method [Wong et al., *J. Neural Transm.* 64:251–269 (1985)]. Briefly, synaptosomal membranes isolated from cerebral cortex were incubated at 37° C. for 10 min. in 2 ml of 50 mM Tris-HCl. pH 7.4; 10 mM pargyline; 0.6 mM ascorbic acid; 5 mM CaCl$_2$; 2 nM $^3$H-8-OH-DPAT and 0.1 to 1000 nm of the compound of interest. Binding was terminated by filtering samples under reduced pressure through glass fiber (GFB) filters. The filters were washed twice with 5 ml of ice cold buffer and placed in scintillation vials with 10 ml of PCS (Amersham/Searle) scintillation fluid. Radioactivity was measured with a liquid scintillation spectrometer. Unlabeled 8-OH-DPAT at 10 μM was also included in separate samples to establish non-specific binding. Specific binding of $^3$H-8-OH-DPAT is defined as the difference of radioactivity bound in the absence and in the presence of 10 μM unlabeled 8-OH-DPAT.

Compounds of this invention were also examined for their in vivo effects on brain 5-HIAA and serum corticosterone levels. Male Sprague-Dawley rats weighting 150–200 g were administered subcutaneously or orally with aqueous solutions of the test compound. One hour after treatment, the rats were decapitated and trunk blood collected. The blood was allowed to clot and then was centrifuged to separate the serum. The concentration of corticosterone in the serum was determined by the spectrofluorometric method of Solem, J. H.; Brinck-Johnsen, T., *Scand. J. Clin. Invest.* [Suppl. 80], 17, 1 (1965). The whole brains from the decapitated rats were quickly removed, frozen on dry ice, and stored at −15° C. 5-HIAA concentrations were measured by liquid chromatography with electrochemical detection as described by Fuller, R. W.; Snoddy, H. D.; Perry, K. W., *Life Sci.* 40, 1921 (1987).

The results of the evaluation of various compounds of the present invention are set forth below in Table I. In Table I, the first column provides the Example Number of the compound evaluated; the second column provides the amount of the test compound expressed in nanomolar concentration required to inhibit the binding of $^3$H-8-OH-DPAT by 50%, indicated as IC$_{50}$; the third column provides the minimum effective dose (MED) of the test compound administered subcutaneously in lowering brain 5-HIAA levels; the fourth column provides the MED of the test compound administered subcutaneously in elevating serum corticosterone levels; and the fifth column provides the same information as the third column except that the test compound is administered orally. The results provided in columns 3–5 are indicative of 5-HT$_{1A}$ agonist activity.

TABLE I

IN VITRO BINDING AND IN VIVO
AGONIST ACTIVITY AT 5-HT$_{1A}$ RECEPTORS

| Example No. | 5-HT1a In vitro binding (IC$_{50}$, nM) | 5-HIAA MED (mg/kg, sc) | Corticosterone MED (mg/kg, sc) | 5-HIAA MED (mg/kg, po) |
|---|---|---|---|---|
| 2 | 36 | | | |
| 5 (5-yl) | 7.2 | | | |
| 5 (3-yl) | 5 | >1.0 | 1.0 | |
| 6 | 62 | | | |
| 8 | 0.44 | 0.1 | 0.3 | 3 |
| 9 | 12 | >1.0 | >1.0 | |
| 10 | 19 | | | |
| 11 | 4.9 | >1.0 | >1.0 | |
| 12 | 87 | | | |
| 13 | 16 | | | |
| 14 | 7.2 | >1.0 | >1.0 | |
| 15 | 33 | | | |
| 16 | 9.8 | >1.0 | >1.0 | |
| 17 | 5 | >1.0 | >1.0 | |
| 20 | 2.5 | >1.0 | >1.0 | |
| 21 | 1.9 | 0.3 | 1.0 | >10 |
| 23 | 1.3 | 1.0 | >1.0 | |
| 24 | 72 | | | |
| 25 | 1.4 | 0.3 | 0.3 | 10 |
| 26 | 6.4 | 1.0 | >1.0 | |
| 28 | 3.8 | >1.0 | >1.0 | |
| 30 | 1.2 | >1.0 | >1.0 | |
| 31 | 1.7 | 1.0 | >1.0 | |
| 32 | 67 | | | |
| 33 | 4.9 | >1.0 | >1.0 | |
| 34 | 11 | | | |
| 35 | 16 | | | |

The compounds of this invention are preferably formulated prior to administration. Therefore, another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of 10 the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl-hydroxybenzoates, propyl hydroxybenzoates, talc, magnesium stearate, and mineral oil. The formulations may additionally include lubricating agents, wetting agents, emulsifying agents, suspending agents, preserving agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 rag, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
|---|---|
| 2-di-n-propylamino-8-(isoxazol-3-yl) 1,2,3,4-tetrahydronaphthalene hydrochloride | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| 2-di-n-propylamino-8-(4-methyl-isoxazol-3-yl)-1,2,3,4-tetrahydronaphthalene hydrochloride | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
|---|---|
| 2-diisopropylamino-8-(1,2,4-oxadiazol-3-yl)-1,2,3,4-tetrahydronaphthalene hydrochloride | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| 2-methylethylamino-8-(thiazol-4-yl)-1,2,3,4-tetrahydronaphthalene maleate | 60 mg |
|---|---|
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| 2-propylamino-8-(5-hydroxypyrazol-3-yl)-1,2,3,4-tetrahydronaphthalene hydrochloride | 80 mg |
|---|---|
| starch | 59 mg |
| microcrystalline cellulose | 59 mg |
| magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| 2-di-n-propylamino-8-(fur-3-yl)-1,2,3,4-tetrahydronaphthalene hydrochloride | 225 mg |
|---|---|
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| 2-diallylamino-8-(3-phenylisoxazol-5-yl)-1,2,3,4-tetrahydronaphthalene hydrochloride | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| 2-diethylamino-8-(isoxazol-5-yl)-1,2,3,4-tetrahydronaphthalene hydrochloride | 100 mg |
| isotonic saline | 1000 ml |

The solution of the above ingredients generally is administered intravenously at a rate of 1 ml per minute to a subject suffering from depression.

We claim:

1. A compound of the formula

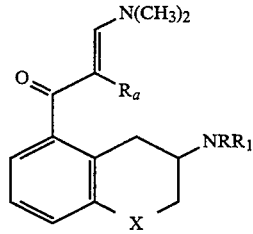

in which R is $C_1$–$C_4$ alkyl, allyl or cyclopropylmethyl;
$R_1$ is hydrogen, $C_1$–$C_4$ alkyl, allyl, cyclopropylmethyl or phenyl ($C_1$–$C_4$ alkyl);
X is —$CH_2$—; and
$R_a$ is hydrogen, $C_1$–$C_4$ alkyl, halogen, hydroxy, $C_1$–$C_4$ alkoxy, $C_1$–$C_4$ alkylthio, amino, cyano or phenyl.

2. Compound of claim 1, in which R and $R_1$ are both $C_1$–$C_4$ alkyl.

3. Compound of claim 2, in which $R_a$ is hydrogen.

4. Compound of claim 3, which compound is 2-di-n-propylamino-8-[1-oxo-3-(dimethylamino)-prop-2-enyl]-1,2,3,4-tetrahydronaphthalene.

* * * * *